US008877188B2

(12) United States Patent
Agarwal et al.

(10) Patent No.: US 8,877,188 B2
(45) Date of Patent: Nov. 4, 2014

(54) DETECTION AND TREATMENT OF NON-DERMAL FIBROSIS

(75) Inventors: Sandeep K. Agarwal, Houston, TX (US); Michael B. Brenner, Newton, MA (US)

(73) Assignees: The Brigham and Women's Hospital, Inc., Boston, MA (US); Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 13/100,528

(22) Filed: May 4, 2011

(65) Prior Publication Data

US 2011/0274703 A1 Nov. 10, 2011

Related U.S. Application Data

(60) Provisional application No. 61/331,355, filed on May 4, 2010.

(51) Int. Cl.
| | |
|---|---|
| A61K 39/395 | (2006.01) |
| A61K 31/00 | (2006.01) |
| C12Q 1/68 | (2006.01) |
| A61K 31/713 | (2006.01) |
| A61K 45/06 | (2006.01) |
| G01N 33/68 | (2006.01) |
| C07K 16/28 | (2006.01) |
| A61K 39/00 | (2006.01) |

(52) U.S. Cl.
CPC ........... *A61K 31/00* (2013.01); *A61K 2039/505* (2013.01); *C12Q 1/6883* (2013.01); *G01N 2333/705* (2013.01); *C12Q 2600/158* (2013.01); *A61K 31/713* (2013.01); *A61K 45/06* (2013.01); *A61K 39/395* (2013.01); *G01N 2800/12* (2013.01); *G01N 33/6884* (2013.01); *C07K 16/28* (2013.01)
USPC ..................................... 424/130.1; 424/143.1

(58) Field of Classification Search
None
See application file for complete search history.

(56) References Cited

U.S. PATENT DOCUMENTS

| | | |
|---|---|---|
| 5,597,725 A | 1/1997 | Suzuki |
| 5,639,634 A | 6/1997 | Suzuki |
| 5,646,250 A | 7/1997 | Suzuki |
| 5,708,143 A | 1/1998 | Suzuki |
| 5,759,808 A | 6/1998 | Casterman et al. |
| 5,798,224 A | 8/1998 | Suzuki |
| 5,877,309 A | 3/1999 | McKay et al. |
| 5,886,026 A | 3/1999 | Hunter et al. |
| 5,891,858 A | 4/1999 | Rubenstein |
| 5,916,807 A | 6/1999 | Bennett et al. |
| 5,929,226 A | 7/1999 | Padmapriya et al. |
| 5,932,557 A | 8/1999 | Mustafa et al. |
| 5,945,290 A | 8/1999 | Cowsert |
| 6,086,877 A | 7/2000 | Nishioka et al. |
| 6,165,745 A | 12/2000 | Ward et al. |
| 6,169,079 B1 | 1/2001 | Bennett et al. |
| 6,433,149 B1 | 8/2002 | Blaschuk et al. |
| 6,472,367 B1 | 10/2002 | Blaschuk et al. |
| 6,787,136 B1 | 9/2004 | Brenner et al. |
| 6,964,768 B2 | 11/2005 | Brenner et al. |
| 7,456,153 B2 | 11/2008 | Blaschuk et al. |
| 7,476,509 B2 | 1/2009 | Blaschuk et al. |
| 7,488,478 B2 | 2/2009 | Brenner et al. |
| 7,589,074 B2 | 9/2009 | Brenner et al. |
| 2004/0175361 A1 | 9/2004 | Blaschuk et al. |
| 2006/0057559 A1 | 3/2006 | Xu et al. |
| 2006/0104972 A1 | 5/2006 | Brenner et al. |
| 2008/0124324 A9 | 5/2008 | Tanha et al. |
| 2008/0214487 A1 | 9/2008 | Brenner et al. |
| 2009/0253200 A1 | 10/2009 | McArthur |
| 2010/0093602 A1 | 4/2010 | Brady-Kalnay et al. |
| 2010/0322926 A1 | 12/2010 | Saint-Mezard |

FOREIGN PATENT DOCUMENTS

| | | |
|---|---|---|
| WO | WO 93/21302 A1 | 10/1993 |
| WO | WO 94/04678 A1 | 3/1994 |
| WO | WO 98/02452 A2 | 1/1998 |
| WO | WO 98/25946 A1 | 6/1998 |
| WO | WO 98/49560 A1 | 11/1998 |
| WO | WO 99/35166 A1 | 7/1999 |
| WO | WO 99/57149 A2 | 11/1999 |
| WO | WO 00/26236 A2 | 5/2000 |
| WO | WO 2004/048411 A2 | 6/2004 |
| WO | WO 2005/007175 A2 | 1/2005 |
| WO | WO 2009/089062 A2 | 7/2009 |
| WO | WO 2009/101059 A2 | 8/2009 |

OTHER PUBLICATIONS

[No Author Listed], Preliminary criteria for the classification of systemic sclerosis (scleroderma). Subcommittee for scleroderma criteria of the American Rheumatism Association Diagnostic and Therapeutic Criteria Committee. Arthritis Rheum. May 1980;23(5):581-90. Abstract Only.

[No Author Listed], Scleroderma Newsbrief. Scleroderma Foundation. 2008. Last Accessed fromhttp://web.archive.org/web/20081006160149/http://www.scleroderma.org/news/news2008/news2008ResearchGrantAwards.shtm on Feb. 11, 2013 4 pages.

Abid et al., Radiation-induced and chemotherapy-induced pulmonary injury. Curr Opin Oncol. Jul. 2001;13(4):242-8. Abstract Only.

Agrawal et al., Antisense therapeutics. Current Opinion in Chemical Biology. 1998;2:519-528.

(Continued)

*Primary Examiner* — Maher Haddad

(74) *Attorney, Agent, or Firm* — Wolf, Greenfield & Sacks, P.C.

(57) ABSTRACT

The invention relates to methods for the diagnosis, prognosis, and treatment of non-dermal fibrosis, including lung (or pulmonary) fibrosis.

7 Claims, 17 Drawing Sheets

(56) References Cited

OTHER PUBLICATIONS

Agrawal, Antisense oligonucleotides: towards clinical trials. Trends Biotechnol. Oct. 1996;14(10):376-87.
Agarwal et al., Coexpression of two mesenchymal cadherins, cadherin 11 and N-cadherin, on murine fibroblast-like synoviocytes. Arthritis Rheum. Apr. 2008;58(4):1044-54. doi: 10.1002/art.23369.
Agarwal et al., Genetics and genomic studies in scleroderma (systemic sclerosis). Rheum Dis Clin North Am. Feb. 2008;34(1):17-40; v. doi: 10.1016/j.rdc.2007.10.001. Abstract Only.
Agarwal et al., Role of adhesion molecules in synovial inflammation. Curr Opin Rheum. 2006;18(3):268-276. Abstract Only.
Ao et al., Injection of Antisense RNA Specific for E-Cadherin Demonstrates that E-Cadherin Facilitates Compaction, the First Differentiative Step of the Mammalian Embryo. Antisense Research and Development. 1992; 2:153-163.
Binkley et al., The molecular basis of pancreatic fibrosis: common stromal gene expression in chronic pancreatitis and pancreatic adenocarcinoma. Pancreas. Nov. 2004;29(4):254-63. Abstract Only.
Branch AD, A good antisense molecule is hard to find. Trends Biochem Sci. Feb. 1998; 23(2):45-50.
Breedveld, F.C, Early rheumatoid arthritis: future treatment. Baillière's Clinical Rheumatology; 1997;11:83-96.
Cepek et al., "Integrin $\alpha^E\beta_7$ Mediates Adhesion of T Lymphocytes to Epithelial Cells", *The Journal of Immunology*, Apr. 15, 1993, pp. 3459-3470, vol. 150, No. 8, Baltimore, MD, USA.
Chitaev et al., "Molecular Organization of the Desmoglein-Plakoglobin Complex", *J Cell Sci.*, Jul. 30, 1998;111 (Pt 14):1941-9.
Costello et al., Dissection of the inflammatory bowel disease transcriptome using genome-wide cDNA microarrays. PLoS Med. Aug. 2005;2(8):e199: 0771-0787. Epub Aug. 23, 2005.
Coultas et al., The epidemiology of interstitial lung diseases. Am J Respir Crit Care Med. Oct. 1994;150(4):967-72. Abstract Only.
Dixit et al., Abrogation of Cisplatin-Induced Programmed Cell Death in Human Breast Cancer Cells by Epidermal Growth Factor Antisense RNA. Journal of the National Cancer Institute. 1997; 89(5):365-372.
Elias et al., New insights into the pathogenesis of asthma. J Clin Invest. Feb. 2003;111(3):291-7.
Falcini et al., "Cadherins Expression in Autoimmune Diseases", *Arthritis Rheum.*, 1997, 40(supp), p. S283. Abstract 1512.
Finck et al., Treatment of Murine Lupus with CTLA4Ig, 1:Science, Aug. 26, 1994;265(5176):1225-7.
Gardner et al., Gene profiling of scleroderma skin reveals robust signatures of disease that are imperfectly reflected in the transcript profiles of explanted fibroblasts. Arthritis Rheum. Jun. 2006;54(6):1961-73.
Getsios et al., Cadherin-11 modulates the terminal differentiation and fusion of human trophoblastic cells in vitro. Developmental Biology. 2003;257: 41-54.
Gorczynski et al., "An Immunoadhesin Incorporating the Molecule OX-2 Is a Potent Immunosuppressant That Prolongs Allo- and Xenograft Survival", *The Journal of Immunology*, 1999, pp. 1654-1660.
Gorczynski et al., "CD200 Immunoadhesin Supresses Collagen-Induced Arthritis in Mice", *Clinical Immunology*, vol. 101, No. 3, December, pp. 328-334, 2001.
Hertzberg, Whole cell assays in screening for biologically active substances. Curr Opin Biotechnol. Feb. 1993;4(1):80-4.
Hoffmann et al., "Cloning and Expression Analysis of a Novel Mesodermally Expressed Cadherin", *Dev Biol.*, May 1995;169(1):337-346.
Jorgensen et al., "In Vivo Migration on Radiolabelled Lymphocytes in Rheumatoid Synovial Tissue Engrafted in SCID Mice: Implication of $\beta2$ and $\beta7$-Integrin", *J. Rheumatol.* 1996, 23:32-5.
Kahan BD, "Immunosuppressive Therapy", *Curr Opin Immunol.*, 4(5):553-560, 1992.
Kiener et al., "Cadherin-11 induces rheumatoid arthritis fibroblast-like synoviocytes to form lining layers in vitro" *Am J Pathol.*, May 2006;168(5):1486-99. Abstract only.
Kuntz, "Structure-Based Strategies for Drug Design and Discovery", *Science*, 1992 257(5073):1078-1082.
Lee et al., "Cadherin-11 in Synovial Lining Formation and Pathology in Arthritis", Science. 2007. 315: 1006-1010.
Lewis et al., Cystic fibrosis. Am J Clin Pathol. Dec. 2003;120 Suppl:S3-13. Abstract Only.
MacCalman et al., "Regulated Expression of Cadherin-11 in Human Epithelial Cells: A Role for Cadherin-11 in Trophoblast-Endometrium Interactions?", *Developmental Dynamics*, 1996, 206:201-211.
Majumdar et al., Different cytokine profiles in cryptogenic fibrosing alveolitis and fibrosing alveolitis associated with systemic sclerosis: a quantitative study of open lung biopsies. Eur Respir J. Aug. 1999;14(2):251-7.
Mareel et al., Cancer metastasis: negative regulation by an invasion-suppressor complex. Cancer Detect Prev. 1995. 19(5): 451-464.
Masur et al., Matrix adhesion characteristics of corneal myofibroblasts. Invest Ophthalmol Vis Sci. Apr. 1999;40(5):904-10.
Mayes et al., Prevalence, incidence, survival, and disease characteristics of systemic sclerosis in a large US population. Arthritis Rheum. Aug. 2003;48(8):2246-55.
Miller et al., "Ligand binding to proteins: The binding landscape model", *Protein Sci.*, 1997, 6:2166-79.
Moeller et al., The bleomycin animal model: a useful tool to investigate treatment options for idiopathic pulmonary fibrosis? Int J Biochem Cell Biol. 2008;40(3):362-82. Epub Aug. 30, 2007. Abstract Only.
Mountain A., "Gene Therapy: The First Decade", *Trends Biotechnol.*, Mar. 2000; 18(3):119-28.
Ngo et al., "Computational Complexity, Protein Structure Prediction, and the Levinthal Paradox", *The Protein Folding Problem and Tertiary Structure Prediction*, ch. 14, pp. 491-494, Birkhauser Boston 1994.
Noë et al., "Inhibition of adhesion and induction of epithelial cell invasion by HAV-containing E-cadherin-specific peptides", *J Cell Sci.* Jan. 1999;112 ( Pt 1):127-35.
Okazaki et al., "Molecular Cloning and Characterization of OB-cadherin, a New Member of Cadherin Family Expressed in Osteoblasts", *The Journal of Biological Chemistry*, vol. 269, No. 16, Apr. 22, 1994, pp. 12092-12098.
Orlandini et al. In fibroblasts Vegf-D expression is induced by cell-cell contact mediated by cadherin-11. Journal of Biological Chemistry. 2001. 276(9): 6576-6581.
Panos et al., Clinical deterioration in patients with idiopathic pulmonary fibrosis: causes and assessment. Am J Med. Apr. 1990;88(4):396-404. Abstract Only.
Piascik et al. Fomiversen Sodium Approved to Treat CMV Retinitis. J. Am Pharm Assoc (Wash). 1999. 39(1):84-85.
Raghu et al., Incidence and prevalence of idiopathic pulmonary fibrosis. Am J Respir Crit Care Med. Oct. 1, 2006;174(7):810-6. Epub Jun. 29, 2006.
Schneider et al., Cadherin-11 contributes to pulmonary fibrosis: potential role in TGF-$\beta$ production and epithelial to mesenchymal transition. FASEB J. Feb. 2012;26(2):503-12. doi:10.1096/fj.11-186098. Epub Oct. 11, 2011.
Selman et al., Idiopathic pulmonary fibrosis: aberrant recapitulation of developmental programs? PLoS Med. Mar. 4, 2008;5(3):e62. doi: 10.1371/journal.pmed.0050062.
Selman et al., Idiopathic pulmonary fibrosis: prevailing and evolving hypotheses about its pathogenesis and implications for therapy. Ann Intern Med. Jan. 16, 2001;134(2):136-51. Abstract Only.
Sime et al., Fibrosis of the lung and other tissues: new concepts in pathogenesis and treatment. Clin Immunol. Jun. 2001;99(3):308-19.
Steen et al., Pulmonary involvement in systemic sclerosis (scleroderma). Arthritis Rheum. Jul. 1985;28(7):759-67. Abstract Only.
Steurer et al., "Ex Vivo Coating of Islet Cell Allografts with Murine CTLA4/Fc Promotes Graft Tolerance", *The American Association of Immunologists*, 1995, pp. 1165-1174.
Suzuki et al., "Diversity of the cadherin family: evidence for eight new cadherins in nervous tissue", *Cell Regulation*, vol. 2, 261-270, Apr. 1991, pp. 261-270.

(56) References Cited

OTHER PUBLICATIONS

Tanihara et al., "Cloning of Five Human Cadherins Clarifies Characteristic Features of Cadherin Extracellular Domain and Provides Further Evidence for Two Structurally Different Types of Cadherin", *Cell Adhesion and Communications*, 1994, pp. 15-26, vol. 2, Harwood Academic Publishers GmbH, USA.

Thannickal et al., Mechanisms of pulmonary fibrosis. Annu Rev Med. 2004;55:395-417. Abstract Only.

Trollmo et al., "Expression of the Mucosal Lymphocyte Integrin $\alpha^E\beta_7$ and its Ligand E-Cadherin in the Synovium of Patients with Rheumatoid Arthritis", *Scand. J. Immunol.*, 1996, 44:293-298.

Valencia et al., "Cadherin-11 Mediates Homophilic Adhesion of Type B Synoviocytes in Rheumatoid Arthritis", *Arthritis & Rheumatism*, Sep. 1999, p. S89, vol. 42, No. 9 suppl., NY, NY, USA, Abstract 111.

Valencia et al., "Identification of Cadherin-11 in Type B Synoviocyters Derived from Rheumatoid Arthritis Patients", *Arthritis & Rheumatism*, vol. 41, No. 9 suppl., Sep. 1998, p. S190, NY, NY, USA. Abstract 946.

Vallin et al., Xenopus cadherin-11 is expressed in different populations of migrating neural crest cells. Mech Dev. Jul. 1998;75(1-2):171-4.

Van Noort et al., "Cell Biology of Autoimmune Diseases", *Int Rev Cytol.*, 1998; 178:127-206.

Vanhee et al., Mechanisms of fibrosis in coal workers' pneumoconiosis. Increased production of platelet-derived growth factor, insulin-like growth factor type I, and transforming growth factor beta and relationship to disease severity. Am J Respir Crit Care Med. Oct. 1994;150(4):1049-55. Abstract Only.

Vleminckx et al., Genetic manipulation of E-cadherin expression by epithelial tumor cells reveals an invasion suppressor role. cell. 1991. 66:107-119.

Wagner, Asbestosis and silicosis. Lancet. May 3, 1997;349(9061):1311-5. Abstract Only.

Wilby et al., "N-Cadherin inhibits Schwann cell migration on astrocytes", *Mol Cell Neurosci.*, Jul. 1999;14(1):66-84.

Wilson, Cost-of-illness of scleroderma: the case for rare diseases. Semin Arthritis Rheum. Oct. 1997;27(2):73-84. Abstract Only.

Yagi et al., Cadherin superfamily genes: functions, genomic organization, and neurologic diversity. Genes Dev. May 15, 2000;14(10):1169-80.

```
                              SEQ ID NO:1
   1 agatgccgcg ggggccgctc gcagccgccg ctgacttgtg aatgggaccg ggactggggc
  61 cgggactgac accgcagcgc ttgccctgcg ccagggactg gcggctcgga ggttgcgtcc
 121 accctcaagg gccccagaaa tcactgtgtt ttcagctcag cggccctgtg acattccttc
 181 gtgttgtcat ttgttgagtg accaatcaga tgggtggagt gtgttacaga aattggcagc
 241 aagtatccaa tgggtgaaga agaagctaac tggggacgtg ggcagccctg acgtgatgag
 301 ctcaaccagc agagacattc catcccaaga gaggtctgcg tgacgcgtcc ggggaggccac
 361 cctcagcaag accaccgtac agttggtgga aggggtgaca gctgcattct cctgtgccta
 421 ccacgtaacc aaaaatgaag gagaactact gtttacaagc cgccctggtg tgcctgggca
 481 tgctgtgcca cagccatgcc tttgccccag agcggcgggg gcacctgcgg ccctccttcc
 541 atgggcacca tgagaagggc aaggagggc aggtgctaca gcgctccaag cgtggctggg
 601 tctggaacca gttcttcgtg atagaggagt acaccgggcc tgaccccgtg cttgtgggca
 661 ggcttcattc agatattgac tctggtgatg ggaacattaa atacattctc tcaggggaag
 721 gagctggaac cattttgtg attgatgaca atcagggaa cattcatgcc accaagacgt
 781 tggatcgaga agagagagcc cagtacacgt tgatggctca ggcggtggac agggacacca
 841 atcggccact ggagccaccg tcggaattca ttgtcaaggt ccaggacatt aatgacaacc
 901 ctccggagtt cctgcacgag acctatcatg ccaacgtgcc tgagaggtcc aatgtgggaa
 961 cgtcagtaat ccaggtgaca gcttcagatg cagatgaccc cacttatgga aatagcgcca
1021 agttagtgta cagtatcctc gaaggacaac cctattttc ggtggaagca cagacaggta
1081 tcatcagaac agccctaccc aacatggaca gggaggccaa ggaggagtac cacgtggtga
1141 tccaggccaa ggacatgggt ggacatatgg gcggactctc agggacaacc aaagtgacga
1201 tcacactgac cgatgtcaat gacaacccac caaagtttcc gcagagcgta taccagatgt
1261 ctgtgtcaga agcagccgtc cctggggagg aagtaggaag agtgaaagct aaagatccag
1321 acattggaga aaatggctta gtcacataca atattgttga tggagatggt atggaatcgt
1381 ttgaaatcac aacggactat gaaacacagg aggggtgat aaagctgaaa aagcctgtag
1441 attttgaaac caaaagagcc tatagcttga aggtagaggc agccaacgtg cacatcgacc
1501 cgaagtttat cagcaatggc cctttcaagg acactgtgac cgtcaagatc tcagtagaag
1561 atgctgatga gcccctatg ttcttggccc caagttacat ccacgaagtc caagaaaatg
1621 cagctgctgg caccgtggtt gggagagtgc atgccaaaga ccctgatgct gccaacagcc
1681 cgataaggta ttccatcgat cgtcacactg acctcgacag attttcact attaatccag
1741 aggatggttt tattaaaact acaaaccctc tggatagaga ggaaacagcc tggctcaaca
1801 tcactgtctt tgcagcagaa atccacaatc ggcatcagga agccaaagtc ccagtggcca
1861 ttagggtcct tgatgtcaac gataatgctc ccaagtttgc tgccccttat gaaggtttca
1921 tctgtgagag tgatcagacc aagccacttt ccaaccagcc aattgttaca attagtgcag
1981 atgacaagga tgacacggcc aatggaccaa gatttatctt cagcctaccc cctgaaatca
2041 ttcacaatcc aaatttcaca gtcagagaca accgagataa cacagcaggc gtgtacgccc
2101 ggcgtggagg gttcagtcgg cagaagcagg acttgtacct tctgcccata gtgatcagcg
2161 atggcggcat cccgcccatg agtagcacca acaccctcac catcaaagtc tgcgggtgcg
2221 acgtgaacgg ggcactgctc tcctgcaacg cagaggccta cattctgaac gccggcctga
2281 gcacaggcgc cctgatcgcc atcctcgcct gcatcgtcat tctcctggtc attgtagtat
2341 tgtttgtgac cctgagaagg caaaagaaag aaccactcat tgtctttgag gaagaagatg
2401 tccgtgagaa catcattact tatgatgatg aagggggtgg ggaagaagac acagaagcct
2461 ttgatattgc caccctccag aatcctgatg gtatcaatgg atttatcccc gcaaagaca
2521 tcaaacctga gtatcagtac atgcctagac ctgggctccg gccagcgccc aacagcgtgg
2581 atgtcgatga cttcatcaac acgagaatac aggaggcaga caatgacccc acggctcctc
2641 cttatgactc cattcaaatc tacggttatg aaggcagggg ctcagtggcc gggtccctga
2701 gctccctaga gtcggccacc acagattcag acttggacta tgattatcta cagaactggg
2761 gacctcgttt taagaaacta gcagatttgt atggtccaa agacactttt gatgacgatt
2821 cttaacaata acgatacaaa tttggcctta agaactgtgt ctggcgttct caagaatcta
2881 gaagatgtgt aaacaggtat ttttttaaat caaggaaagg ctcatttaaa acaggcaaag
2941 ttttacagag aggatacatt taataaaact gcgaggacat caaagtggta aatactgtga
3001 aataccttt ctcacaaaaa ggcaaatatt gaagttgttt atcaactcg ctagaaaaaa
3061 aaaacacttg gcatacaaaa tatttaagtg aaggagaagt ctaacgctca actgacaatg
3121 aagggaaatt gtttatgtgt tatgaacatc caagtctttc ttcttttta agttgtcaaa
```

Fig. 15

```
3181  gaagcttcca  caaaattaga  aaggacaaca  gttctgagct  gtaatttcgc  cttaaactct
3241  ggacactcta  tatgtagtgc  atttttaaac  ttgaaatata  taatattcag  ccagcttaaa
3301  cccatacaat  gtatgtacaa  tacaatgtac  aattatgtct  cttgagcatc  aatcttgtta
3361  ctgctgattc  ttgtaaatct  ttttgcttct  actttcatct  taaactaata  cgtgccagat
3421  ataactgtct  tgtttcagtg  agagacgccc  tatttctatg  tcatttttaa  tgtatctatt
3481  tgtacaattt  taaagttctt  attttagtat  acgtataaat  atcagtattc  tgacatgtaa
3541  gaaaatgtta  cggcatcaca  cttatatttt  atgaacattg  tactgttgct  ttaatatgag
3601  cttcaatata  agaagcaatc  tttgaaataa  aaaaagattt  ttttttaaaa  aaaa
```

Fig. 15 Cont.

SEQ ID NO:2

MKENYCLQAALVCLGMLCHSHAFAPERRGHLRPSFHGHHEKGKE

GQVLQRSKRGWVWNQFFVIEEYTGPDPVLVGRLHSDIDSGDGNIKYILSGEGAGTIFV

IDDKSGNIHATKTLDREERAQYTLMAQAVDRDTNRPLEPPSEFIVKVQDINDNPPEFL

HETYHANVPERSNVGTSVIQVTASDADDPTYGNSAKLVYSILEGQPYFSVEAQTGIIR

TALPNMDREAKEEYHVVIQAKDMGGHMGGLSGTTKVTITLTDVNDNPPKFPQSVYQMS

VSEAAVPGEEVGRVKAKDPDIGENGLVTYNIVDGDGMESFEITTDYETQEGVIKLKKP

VDFETKRAYSLKVEAANVHIDPKFISNGPFKDTVTVKISVEDADEPPMFLAPSYIHEV

QENAAAGTVVGRVHAKDPDAANSPIRYSIDRHTDLDRFFTINPEDGFIKTTKPLDREE

TAWLNITVFAAEIHNRHQEAKVPVAIRVLDVNDNAPKFAAPYEGFICESDQTKPLSNQ

PIVTISADDKDDTANGPRFIFSLPPEIIHNPNFTVRDNRDNTAGVYARRGGFSRQKQD

LYLLPIVISDGGIPPMSSTNTLTIKVCGCDVNGALLSCNAEAYILNAGLSTGALIAIL

ACIVILLVIVVLFVTLRRQKKEPLIVFEEEDVRENIITYDDEGGGEEDTEAFDIATLQ

NPDGINGFIPRKDIKPEYQYMPRPGLRPAPNSVDVDDFINTRIQEADNDPTAPPYDSI

QIYGYEGRGSVAGSLSSLESATTDSDLDYDYLQNWGPRFKKLADLYGSKDTFDDDS

Fig. 16

SEQUENCE LISTING

```
<160> NUMBER OF SEQ ID NOS: 4

<210> SEQ ID NO 1
<211> LENGTH: 3654
<212> TYPE: DNA
<213> ORGANISM: H. sapiens
```

<400> SEQUENCE: 1

```
agatgccgcg ggggccgctc gcagccgccg ctgacttgtg aatgggaccg ggactggggc     60
cgggactgac accgcagcgc ttgccctgcg ccagggactg gcggctcgga ggttgcgtcc    120
accctcaagg gccccagaaa tcactgtgtt ttcagctcag cggccctgtg acattccttc    180
gtgttgtcat ttgttgagtg accaatcaga tgggtggagt gtgttacaga aattggcagc    240
aagtatccaa tgggtgaaga agaagctaac tggggacgtg ggcagccctg acgtgatgag    300
ctcaaccagc agagacattc catcccaaga gaggtctgcg tgacgcgtcc gggaggccac    360
cctcagcaag accaccgtac agttggtgga aggggtgaca gctgcattct cctgtgccta    420
ccacgtaacc aaaaatgaag gagaactact gtttacaagc cgccctggtg tgcctgggca    480
tgctgtgcca cagccatgcc tttgccccag agcggcgggg gcacctgcgg ccctccttcc    540
atgggcacca tgagaagggc aaggaggggc aggtgctaca gcgctccaag cgtggctggg    600
tctggaacca gttcttcgtg atagaggagt acaccgggcc tgaccccgtg cttgtgggca    660
ggcttcattc agatattgac tctggtgatg ggaacattaa atacattctc tcaggggaag    720
gagctggaac cattttttgtg attgatgaca aatcagggaa cattcatgcc accaagacgt    780
tggatcgaga agagagagcc cagtacacgt tgatggctca ggcggtggac agggacacca    840
atcggccact ggagccaccg tcggaattca ttgtcaaggt ccaggacatt aatgacaacc    900
ctccggagtt cctgcacgag acctatcatg ccaacgtgcc tgagaggtcc aatgtgggaa    960
cgtcagtaat ccaggtgaca gcttcagatg cagatgaccc cacttatgga aatagcgcca   1020
agttagtgta cagtatcctc gaaggacaac cctatttttc ggtggaagca cagacaggta   1080
tcatcagaac agccctaccc aacatggaca gggaggccaa ggaggagtac cacgtggtga   1140
tccaggccaa ggacatgggt ggacatatgg gcggactctc agggacaacc aaagtgacga   1200
tcacactgac cgatgtcaat gacaacccac caaagtttcc gcagagcgta taccagatgt   1260
ctgtgtcaga agcagccgtc cctggggagg aagtaggaag agtgaaagct aaagatccag   1320
acattggaga aaatggctta gtcacataca atattgttga tggagatggt atggaatcgt   1380
ttgaaatcac aacggactat gaaacacagg agggggtgat aaagctgaaa aagcctgtag   1440
attttgaaac caaaagagcc tatagcttga aggtagaggc agccaacgtg cacatcgacc   1500
cgaagtttat cagcaatggc cctttcaagg acactgtgac cgtcaagatc tcagtagaag   1560
atgctgatga gccccctatg ttcttggccc caagttacat ccacgaagtc caagaaaatg   1620
cagctgctgg caccgtggtt gggagagtgc atgccaaaga ccctgatgct gccaacagcc   1680
cgataaggta ttccatcgat cgtcacactg acctcgacag attttttcact attaatccag   1740
aggatggttt tattaaaact acaaaaacctc tggatagaga ggaaacagcc tggctcaaca   1800
tcactgtctt tgcagcagaa atccacaatc ggcatcagga agccaaagtc ccagtggcca   1860
ttagggtcct tgatgtcaac gataatgctc ccaagtttgc tgcccccttat gaaggtttca   1920
tctgtgagag tgatcagacc aagccacttt ccaaccagcc aattgttaca attagtgcag   1980
atgacaagga tgcacacggcc aatggaccaa gatttatctt cagcctaccc cctgaaatca   2040
ttcacaatcc aaatttcaca gtcagagaca accgagataa cacagcaggc gtgtacgccc   2100
ggcgtggagg gttcagtcgg cagaagcagg acttgtacct tctgcccata gtgatcagcg   2160
atggcggcat cccgcccatg agtagcacca acaccctcac catcaaagtc tgcgggtgcg   2220
acgtgaacgg ggcactgctc tcctgcaacg cagaggccta cattctgaac gccggcctga   2280
```

```
gcacaggcgc cctgatcgcc atcctcgcct gcatcgtcat tctcctggtc attgtagtat    2340
tgtttgtgac cctgagaagg caaaagaaag aaccactcat tgtctttgag gaagaagatg    2400
tccgtgagaa catcattact tatgatgatg aagggggtgg ggaagaagac acagaagcct    2460
ttgatattgc caccctccag aatcctgatg gtatcaatgg atttatcccc cgcaaagaca    2520
tcaaacctga gtatcagtac atgcctagac ctgggctccg gccagcgccc aacagcgtgg    2580
atgtcgatga cttcatcaac acgagaatac aggaggcaga caatgacccc acggctcctc    2640
cttatgactc cattcaaatc tacggttatg aaggcagggg ctcagtggcc gggtccctga    2700
gctccctaga gtcggccacc acagattcag acttggacta tgattatcta cagaactggg    2760
gacctcgttt taagaaacta gcagatttgt atggttccaa agacactttt gatgacgatt    2820
cttaacaata cgatacaaa tttggcctta agaactgtgt ctggcgttct caagaatcta    2880
gaagatgtgt aaacaggtat ttttttaaat caaggaaagg ctcatttaaa acaggcaaag    2940
ttttacagag aggatacatt taataaaact gcgaggacat caaagtggta atactgtga    3000 aataccttt ctcacaaaaa ggcaaatatt gaagttgttt atcaacttcg ctagaaaaaa    3060
aaaacacttg gcatacaaaa tatttaagtg aaggagaagt ctaacgctga actgacaatg    3120
aagggaaatt gtttatgtgt tatgaacatc caagtctttc ttctttttta agttgtcaaa    3180
gaagcttcca caaaattaga aaggacaaca gttctgagct gtaatttcgc cttaaactct    3240
ggacactcta tatgtagtgc attttttaaac ttgaaatata taatattcag ccagcttaaa    3300
cccatacaat gtatgtacaa tacaatgtac aattatgtct cttgagcatc aatcttgtta    3360
ctgctgattc ttgtaaatct ttttgcttct actttcatct taaactaata cgtgccagat    3420
ataactgtct tgtttcagtg agagacgccc tatttctatg tcatttttaa tgtatctatt    3480
tgtacaattt taaagttctt attttagtat acgtataaat atcagtattc tgacatgtaa    3540
gaaaatgtta cggcatcaca cttatatttt atgaacattg tactgttgct ttaatatgag    3600
cttcaatata agaagcaatc tttgaaataa aaaagatttt tttttaaaa aaaa          3654
```

<210> SEQ ID NO 2
<211> LENGTH: 796
<212> TYPE: PRT
<213> ORGANISM: H. sapiens

<400> SEQUENCE: 2

```
Met Lys Glu Asn Tyr Cys Leu Gln Ala Ala Leu Val Cys Leu Gly Met
 1               5                  10                  15

Leu Cys His Ser His Ala Phe Ala Pro Glu Arg Arg Gly His Leu Arg
            20                  25                  30

Pro Ser Phe His Gly His His Glu Lys Gly Lys Glu Gly Gln Val Leu
        35                  40                  45

Gln Arg Ser Lys Arg Gly Trp Val Trp Asn Gln Phe Phe Val Ile Glu
    50                  55                  60

Glu Tyr Thr Gly Pro Asp Pro Val Leu Val Gly Arg Leu His Ser Asp
65                  70                  75                  80

Ile Asp Ser Gly Asp Gly Asn Ile Lys Tyr Ile Leu Ser Gly Glu Gly
                85                  90                  95

Ala Gly Thr Ile Phe Val Ile Asp Asp Lys Ser Gly Asn Ile His Ala
            100                 105                 110

Thr Lys Thr Leu Asp Arg Glu Glu Arg Ala Gln Tyr Thr Leu Met Ala
        115                 120                 125

Gln Ala Val Asp Arg Asp Thr Asn Arg Pro Leu Glu Pro Pro Ser Glu
```

```
            130                 135                 140
    Phe Ile Val Lys Val Gln Asp Ile Asn Asp Asn Pro Pro Glu Phe Leu
    145                 150                 155                 160

His Glu Thr Tyr His Ala Asn Val Pro Glu Arg Ser Asn Val Gly Thr
                    165                 170                 175

Ser Val Ile Gln Val Thr Ala Ser Ala Asp Asp Pro Thr Tyr Gly
                    180                 185                 190

Asn Ser Ala Lys Leu Val Tyr Ser Ile Leu Glu Gly Gln Pro Tyr Phe
                    195                 200                 205

Ser Val Glu Ala Gln Thr Gly Ile Ile Arg Thr Ala Leu Pro Asn Met
    210                 215                 220

Asp Arg Glu Ala Lys Glu Tyr His Val Val Ile Gln Ala Lys Asp
    225                 230                 235                 240

Met Gly Gly His Met Gly Gly Leu Ser Gly Thr Thr Lys Val Thr Ile
                    245                 250                 255

Thr Leu Thr Asp Val Asn Asp Asn Pro Pro Lys Phe Pro Gln Ser Val
                    260                 265                 270

Tyr Gln Met Ser Val Ser Glu Ala Ala Val Pro Gly Glu Glu Val Gly
                    275                 280                 285

Arg Val Lys Ala Lys Asp Pro Asp Ile Gly Glu Asn Gly Leu Val Thr
                    290                 295                 300

Tyr Asn Ile Val Asp Gly Asp Gly Met Glu Ser Phe Glu Ile Thr Thr
    305                 310                 315                 320

Asp Tyr Glu Thr Gln Glu Gly Val Ile Lys Leu Lys Lys Pro Val Asp
                    325                 330                 335

Phe Glu Thr Lys Arg Ala Tyr Ser Leu Lys Val Glu Ala Ala Asn Val
                    340                 345                 350

His Ile Asp Pro Lys Phe Ile Ser Asn Gly Pro Phe Lys Asp Thr Val
                    355                 360                 365

Thr Val Lys Ile Ser Val Glu Asp Ala Asp Glu Pro Pro Met Phe Leu
                    370                 375                 380

Ala Pro Ser Tyr Ile His Glu Val Gln Glu Asn Ala Ala Ala Gly Thr
    385                 390                 395                 400

Val Val Gly Arg Val His Ala Lys Asp Pro Asp Ala Ala Asn Ser Pro
                    405                 410                 415

Ile Arg Tyr Ser Ile Asp Arg His Thr Asp Leu Asp Arg Phe Phe Thr
                    420                 425                 430

Ile Asn Pro Glu Asp Gly Phe Ile Lys Thr Thr Lys Pro Leu Asp Arg
                    435                 440                 445

Glu Glu Thr Ala Trp Leu Asn Ile Thr Val Phe Ala Ala Glu Ile His
                    450                 455                 460

Asn Arg His Gln Glu Ala Lys Val Pro Val Ala Ile Arg Val Leu Asp
    465                 470                 475                 480

Val Asn Asp Asn Ala Pro Lys Phe Ala Ala Pro Tyr Glu Gly Phe Ile
                    485                 490                 495

Cys Glu Ser Asp Gln Thr Lys Pro Leu Ser Asn Gln Pro Ile Val Thr
                    500                 505                 510

Ile Ser Ala Asp Asp Lys Asp Thr Ala Asn Gly Pro Arg Phe Ile
                    515                 520                 525

Phe Ser Leu Pro Pro Glu Ile Ile His Asn Pro Asn Phe Thr Val Arg
                    530                 535                 540

Asp Asn Arg Asp Asn Thr Ala Gly Val Tyr Ala Arg Arg Gly Gly Phe
    545                 550                 555                 560
```

```
Ser Arg Gln Lys Gln Asp Leu Tyr Leu Leu Pro Ile Val Ile Ser Asp
                565                 570                 575

Gly Gly Ile Pro Pro Met Ser Ser Thr Asn Thr Leu Thr Ile Lys Val
            580                 585                 590

Cys Gly Cys Asp Val Asn Gly Ala Leu Leu Ser Cys Asn Ala Glu Ala
        595                 600                 605

Tyr Ile Leu Asn Ala Gly Leu Ser Thr Gly Ala Leu Ile Ala Ile Leu
    610                 615                 620

Ala Cys Ile Val Ile Leu Leu Val Ile Val Leu Phe Val Thr Leu
625                 630                 635                 640

Arg Arg Gln Lys Lys Glu Pro Leu Ile Val Phe Glu Glu Glu Asp Val
                645                 650                 655

Arg Glu Asn Ile Ile Thr Tyr Asp Asp Glu Gly Gly Gly Glu Glu Asp
            660                 665                 670

Thr Glu Ala Phe Asp Ile Ala Thr Leu Gln Asn Pro Asp Gly Ile Asn
        675                 680                 685

Gly Phe Ile Pro Arg Lys Asp Ile Lys Pro Glu Tyr Gln Tyr Met Pro
    690                 695                 700

Arg Pro Gly Leu Arg Pro Ala Pro Asn Ser Val Asp Val Asp Asp Phe
705                 710                 715                 720

Ile Asn Thr Arg Ile Gln Glu Ala Asp Asn Asp Pro Thr Ala Pro Pro
                725                 730                 735

Tyr Asp Ser Ile Gln Ile Tyr Gly Tyr Glu Gly Arg Gly Ser Val Ala
            740                 745                 750

Gly Ser Leu Ser Ser Leu Glu Ser Ala Thr Thr Asp Ser Asp Leu Asp
        755                 760                 765

Tyr Asp Tyr Leu Gln Asn Trp Gly Pro Arg Phe Lys Lys Leu Ala Asp
    770                 775                 780

Leu Tyr Gly Ser Lys Asp Thr Phe Asp Asp Ser
785                 790                 795

<210> SEQ ID NO 3
<211> LENGTH: 34
<212> TYPE: PRT
<213> ORGANISM: H. sapiens

<400> SEQUENCE: 3

Gly Trp Val Trp Asn Gln Phe Phe Val Ile Glu Glu Tyr Thr Gly Pro
1               5                   10                  15

Asp Pro Val Leu Val Gly Arg Leu His Ser Asp Ile Asp Ser Gly Asp
            20                  25                  30

Gly Asn

<210> SEQ ID NO 4
<211> LENGTH: 21
<212> TYPE: RNA
<213> ORGANISM: artificial sequence
<220> FEATURE:
<223> OTHER INFORMATION: human Cdh11 siRNA

<400> SEQUENCE: 4
uuugaaugga gucauaaggu u                                           21
```

DETECTION AND TREATMENT OF NON-DERMAL FIBROSIS

RELATED APPLICATIONS

This application claims benefit under 35 U.S.C. §119(e) to U.S. Provisional Application No. 61/331,355, filed May 4, 2010, entitled "DETECTION AND TREATMENT OF NON-DERMAL FIBROSIS", the entire contents of which are incorporated by reference.

FEDERALLY SPONSORED RESEARCH

This invention was made with Government support under grant number RO1 AR048114 from the National Institutes of Health. The Government has certain rights to this invention.

FIELD OF THE INVENTION

The invention provides methods for diagnosing, monitoring and treating non-dermal fibrosis by interfering with cadherin-11 activity.

BACKGROUND OF INVENTION

Interstitial lung diseases, now known as diffuse proliferative lung diseases, are a spectrum of diffuse parenchymal lung disease that is characterized by variable degrees of pulmonary fibrosis[3]. Pulmonary fibrosis is a component of various interstitial pneumonias[3]. These disorders are characterized by varying degrees of inflammation, aberrant fibroblast proliferation, and extracellular matrix deposition that result in distortion of pulmonary architecture that compromises pulmonary function[3, 4]. There are many causes of pulmonary fibrosis including exposure to fibrosis-inducing agents such as silica[5], coal dust[6], radiation[7] and certain chemotherapeutic agents[7]. Despite its prevalence, the pathogenesis of pulmonary fibrosis is not completely understood and treatment options for the resolution of pulmonary fibrosis are lacking.

Approximately 35% of interstitial lung diseases can be grouped into a condition known as idiopathic pulmonary fibrosis (IPF)[12]. A comprehensive epidemiological study investigating the incidence of IPF, revealed a general prevalence rate of approximately 20 cases per 100,000[12]. This incidence was higher in individuals over 75 years of age where 175 cases per 100,000 were noted. A more recent study demonstrated a prevalence of approximately 43 cases per 100,000 and an incidence of 16.3 cases per 100,000 patient years.[13] These data suggest that the incidence and prevalence of IPF in on the rise. IPF is a chronic and particularly devastating form of interstitial lung disease. It is largely untreatable and leads to death within 3 to 8 years of diagnosis[14]. There are no effective disease-modifying treatments for IPF.

SUMMARY OF INVENTION

The invention is premised, in part, on the unexpected finding that cadherin-11 is involved in non-dermal fibrotic conditions (i.e., non-dermal fibrosis), and that as a result cadherin-11 is a diagnostic marker, prognostic marker and therapeutic target for such conditions. As described in greater detail herein, cadherin-11 was found to be upregulated in non-dermal fibrotic tissues including in alveolar macrophages and alveolar epithelial cells found in bronchoalveolar lavage, and subjects lacking cadherin-11 were found to be less susceptible to experimentally-induced non-dermal fibrosis, such as lung fibrosis. Accordingly, the invention provides compositions and methods for diagnosing, monitoring and treating non-dermal fibrosis, including in particular lung fibrosis.

Thus, in one aspect, the invention provides a method for treating a subject at risk of developing non-dermal fibrosis comprising administering to said subject a cadherin-11 antagonist in an amount effective to prevent or delay the onset of symptoms associated with non-dermal fibrosis.

The invention provides, in another aspect, a method for treating a subject having non-dermal fibrosis comprising administering to a subject in need thereof a cadherin-11 antagonist in an amount effective to reduce non-dermal fibrosis.

In one embodiment, the non-dermal fibrosis is lung fibrosis or liver fibrosis. In an important embodiment, the non-dermal fibrosis is lung fibrosis, more specifically idiopathic pulmonary fibrosis, and even more specifically severe idiopathic pulmonary fibrosis.

In one embodiment, the cadherin-11 antagonist is a cadherin-11 binding peptide. In one embodiment, the cadherin-11 binding peptide is an anti-cadherin-11 antibody or an antigen-binding antibody fragment. In one embodiment, the cadherin-11 binding peptide is a cadherin-11 fusion protein. In one embodiment, the cadherin-11 binding peptide comprises full length cadherin or a fragment thereof.

In one embodiment, the cadherin-11 antagonist is a cadherin-11 nucleic acid antagonist. In one embodiment, the cadherin-11 nucleic acid antagonist is a cadherin-11 siRNA. In one embodiment, the cadherin-11 nucleic acid antagonist is a cadherin-11 ribozyme. In one embodiment, the cadherin-11 nucleic acid antagonist is a cadherin-11 antisense molecule. In one embodiment, cadherin-11 nucleic acid antagonist is a nucleic acid encoding full length cadherin-11 or a fragment thereof. In one embodiment, cadherin-11 nucleic acid antagonist is an aptamer.

In one embodiment, the cadherin-11 antagonist is a small molecule.

In one embodiment, the cadherin-11 antagonist is administered by inhalation or intranasally. In one embodiment, the cadherin-11 antagonist is administered intraperitoneally.

In one embodiment, the method further comprises administering a second therapeutic agent to the subject. In one embodiment, the second therapeutic agent is an immunosuppressant. In one embodiment, the immunosuppressant is a steroid.

In another aspect, the invention provides a method comprising measuring cadherin-11 level in a sample harvested from a subject, and comparing the cadherin-11 level in the sample with a normal control, wherein a cadherin-11 level in the sample harvested from the subject that is greater than the cadherin-11 level in the normal control indicates non-dermal fibrosis or a risk of developing non-dermal fibrosis.

The cadherin-11 level may be measured by manipulating the sample such as for example by lysing cells of the sample and detecting cadherin-11 expression products therein. In one embodiment, the cadherin-11 level is a cadherin-11 protein level. In one embodiment, the cadherin-11 level is a cadherin-11 mRNA level.

In one embodiment, the normal control is a sample of normal tissue or cells from the subject. In one embodiment, the normal control is a level of cadherin-11 in a population of subjects.

In one embodiment, the sample is a lung sample. In one embodiment, the sample is a bronchoalveolar lavage (BAL) sample. In one embodiment, the sample comprises alveolar macrophages and/or alveolar epithelial cells. In one embodiment, the sample is a liver sample.

In one embodiment, cadherin-11 level is measured using immunohistochemistry.

In one embodiment, a cadherin-11 level in the sample harvested from the subject that is greater than the normal control indicates the subject has non-dermal fibrosis.

In one embodiment, a cadherin-11 level in the sample harvested from the subject that is greater than the normal control indicates the subject is at risk of developing non-dermal fibrosis.

In another aspect, the invention provides a method for inhibiting development (or differentiation) of myofibroblasts from fibroblasts using cadherin-11 antagonists. In important embodiments, fibroblast-to-myofibroblast differentiation is associated with development of non-dermal fibrosis. The degree of inhibition may be determined by measuring the absolute or relative number or percentage of myofibroblasts following contact with the cadherin-11 antagonist. In some instances, inhibiting may include delaying (or slowing the kinetics of) myofibroblast development.

In another aspect, the invention provides a method for inhibiting an epithelial-to-mesenchymal transition (EMT). In important embodiments, the EMT is associated with development of non-dermal fibrosis. In some instances, inhibiting may include delaying (or slowing the kinetics of) EMT. Markers of EMT include phenotype (e.g., loss of epithelial cell polarity, separation of cells from each other, expression of growth factors, (e.g., TGF-beta and wnt), expression of transcription factors (e.g., SNAILS, SMAD, LEF, and nuclear beta-catenin), expression of cell adhesion molecules (e.g., E-cadherin), and the like. These markers are known to those of ordinary skill in the art.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF DRAWINGS

It is to be understood that the Figures are not necessarily to scale, emphasis instead being placed upon generally illustrating the various concepts discussed herein.

FIG. 15. Nucleotide sequence of human cadherin-11 (SEQ ID NO:1).

FIG. 16. Amino acid sequence of human cadherin-11 (SEQ ID NO:2).

DETAILED DESCRIPTION OF INVENTION

Figure 1:
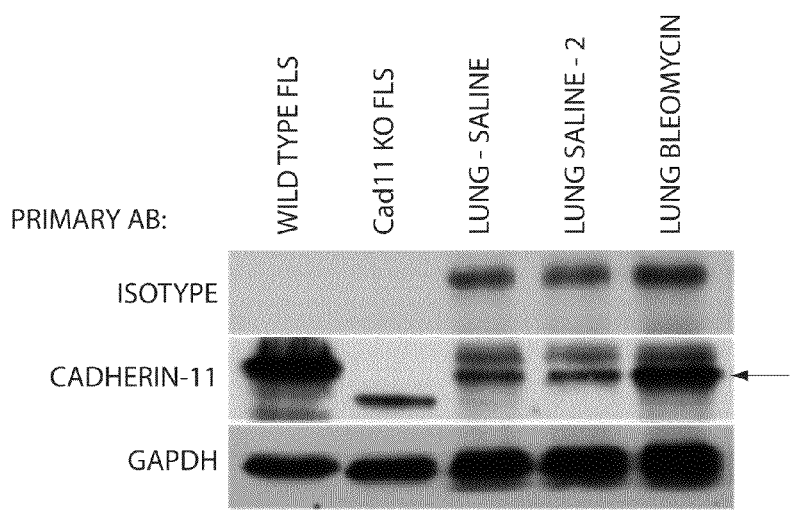
FIG. 1. Protein lysates were isolated from lungs of wild type mice administered saline or bleomycin via the intratracheal route. Lungs were harvested on day 12. Protein lysates were separated on a 10% acrylamide gel by electrophoresis, then transfer to a membrane for western blotting using isotype control antibody, anti-cadherin-11 antibody (Invitrogen) or anti-GAPDH antibody. Wild type and cadherin-11 null fibroblast-like synoviocytes were used as positive and negative controls for the expression of cadherin-11. The bleomycin lung had increased levels of cadherin-11 but similar levels of GAPDH, indicating that cadherin-11 is increased during the process of lung fibrosis.

The invention is based, in part, on the unexpected finding that cadherin-11 is upregulated in non-dermal fibrosis (such as pulmonary fibrosis), and that the lack of cadherin-11 provides some resistance to experimentally-induced non-dermal fibrosis (such as pulmonary fibrosis). Included in these findings is the further unexpected discovery that alveolar macrophages and alveolar epithelial cells express cadherin-11 in these experimental models and thus these cells may be analyzed to detect and/or monitor fibrosis. Importantly, these cells are present in bronchoalveolar lavage and thus detection and/or monitoring assays for lung fibrosis can be performed using BAL samples rather than an invasive procedure. Based on these findings, the invention contemplates and provides compositions and methods for the treatment of non-dermal fibrosis comprising cadherin-11 antagonists. The accompanying Examples demonstrate, inter alia, that lung tissue from patients with severe idiopathic pulmonary fibrosis have increased levels of cadherin-11, and that mice having experimentally-induced lung fibrosis also have increased levels of cadherin-11. Most strikingly, mice lacking cadherin-11 (i.e., cadherin-11 knock-out mice) have decreased tissue fibrosis in the lung in this same experimental model. The Examples further show that anti-cadherin-11 antibodies are effective in treating pulmonary fibrosis even after it is established. These data are the first evidence that, inter alia, cadherin-11 is not only a key mediator of non-dermal fibrosis but also a therapeutic target in the treatment of non-dermal fibrosis, including pulmonary fibrosis.

Fibrosis:

Fibrosis refers to the development of excess fibrous connective tissue in an organ or tissue. Fibrosis can occur in a variety of tissues or organs. Fibrotic conditions include lung fibrosis, hepatic fibrosis (e.g., associated with alcohol consumption, viral hepatitis, and/or schistosomiasis), hypertrophic scars, keloids, burns, Peyronie's disease, Dupuytren's contractures, myelofibrosis, pancreatic fibrosis, post-myocardial infarction cardiac fibrosis, kidney/renal fibrosis associated with diabetes, post-inflammatory renal fibrosis, and drug-induced fibrosis (e.g., resulting from chemotherapy and/or radiation exposure).

Important aspects of the invention intend to diagnose, monitor and/or treat non-dermal fibrosis. Non-dermal fibrosis is fibrosis that manifests itself in an organ other than the skin (or dermis). As important example of non-dermal fibrosis is lung (or pulmonary) fibrosis. Lung fibrosis can be associated with interstitial lung disease and diffuse proliferative lung disease. An more specific example of lung fibrosis is idiopathic pulmonary fibrosis (IPF), including IPF with severe airway restriction (referred to herein as severe IPF). Other examples of non-dermal fibrosis include liver (or hepatic) fibrosis, ocular fibrosis, fibrosis of the gut, kidney (or renal) fibrosis, pancreatic fibrosis, and vascular fibrosis. Some forms of non-dermal fibrosis are referred to as non-dermal interstitial fibrosis.

Non-dermal fibrosis may be further categorized by its etiology, to the extent such etiology is known. For example, the fibrosis, including non-dermal fibrosis, may be associated with or resulting from an infection (e.g., a viral infection or a parasitic infection), or it may be drug-induced fibrosis (e.g., chemotherapy), or it may be alcohol-induced fibrosis.

Non-dermal fibrosis may be transplant-induced or it may occur independently of transplant (i.e., in a subject that has not undergone a transplant and who is not in need of a transplant). In some embodiments of the invention, the subject has not undergone a kidney (or renal transplant) nor is the subject in need of such a transplant. In still other embodiments, the subject has not undergone a heart transplant nor is the subject in need of such a transplant. In still other embodiments, the subject does not have and/or is not at an elevated risk of developing an inflammatory joint disorder such as rheumatoid arthritis. In still other embodiments, the subjects do not have a cancer and/or are not at an elevated risk of developing cancer.

The invention intends to detect (e.g., diagnose) and/or treat (including prevent) non-dermal fibrosis in any subject having or susceptible to having non-dermal fibrosis. The subjects may be human and non-human subjects. Non-human subjects include but are not limited to companion animals (e.g., dogs and cats), agricultural or competitive animals (e.g., cows, horses, etc.).

It is to be understood that the invention contemplates methods for detecting non-dermal fibrosis based on the presence of abnormally elevated levels of cadherin-11 in a tissue or in cells. Such methods may be diagnostic in nature (i.e., they may indicate, alone or together with other symptoms or manifestations that the subject has non-dermal fibrosis) or they may be prognostic in nature (i.e., they may indicate, alone or with patient history information, that the subject is likely to develop non-dermal fibrosis). The invention further contemplates treating a subject having or at risk of developing fibrosis by administering to such subject a cadherin-11 antagonist, as described in greater detail herein.

Cadherin-11:

Cadherin-11 is a classical type II cadherin. It comprises a short intracellular domain, a transmembrane domain, and an extracellular domain. The extracellular domain is comprised of 5 subdomains (sometimes themselves referred to as domains), each of which consists of about 110 amino acids. The human and mouse cadherin-11 genes have been isolated and sequenced previously (Suzuki S. et al. Cell Reg 2:261-70, 1991). See also, Genbank Accession No. NM_001797, for the human cadherin-11 cDNA and predicted amino acid sequences (SEQ ID NO: 1 and SEQ ID NO: 2), respectively. Cadherin-11 is also referred to as OB-cadherin, osteoblast cadherin, OSF-4, and CDH11.

The main function of cadherins is to facilitate the adhesion of one cell to another, sometimes similar, cell. Cadherins are involved in cell-to-cell contact and cellular invasion during embryogenesis. In the post-natal tissue, they serve to maintain cell-to-cell contact in epithelial structures. Cadherins likely have other functions beyond cell-to-cell adhesion. For example, as described in the Examples, cadherin-11 is involved in epithelial-to-mesenchymal transition (EMT) during development of non-dermal fibrosis. Also, as shown in the Examples, cadherin-11 is involved in the differentiation of myofibroblasts from fibroblasts.

Cadherin-11 Antagonists:

As used herein, the term antagonist refers to any protein, polypeptide, peptide, peptidomimetic, glycoprotein, antibody, antibody fragment, carbohydrate, nucleic acid, organic molecule, inorganic molecule, large molecule, or small molecule that blocks, inhibits, reduces or neutralizes the function, activity and/or expression of another molecule. As used herein, a cadherin-11 antagonist is an agent that blocks, inhibits, reduces or neutralizes the function, activity and/or expression of cadherin-11. As described above, cadherin-11 is involved in cell attachment, interaction and/or migration. Cadherin-11 is known to bind to itself in what is referred to as homophilic or homotypic binding. The cadherin-11 antagonists may interfere with cadherin-11 homotypic binding or heterotypic binding (i.e., binding of cadherin-11 to a counter-receptor that is not cadherin-11). The cadherin-11 antagonist may interfere with cadherin-11 function by reducing the amount of cadherin-11 that is expressed by a cell or by interacting with cadherin-11 (or its counter-receptor) thereby preventing interaction of cadherin-11 with its target. Accordingly, the cadherin-11 antagonist may interfere, in whole or in part, with the transcription of cadherin-11 or with the translation of cadherin-11 (thereby interfering with cadherin-11 expression), or it may interfere with the ability of cadherin-11 to bind to another cadherin-11 or to another cadherin-11 counter-receptor. The cadherin-11 antagonist may reduce cadherin-11 function or activity by about 10%, 20%, 30%, 40%, 50%, 60%, 70%, 80%, 90% or 100%, relative to a control such as PBS. It will be understood that the cadherin-11 antagonist may be used in an amount that reduces cadherin-11 function or activity by about these amounts. It will further be understood that some cadherin-11 antagonists are preferably used in vitro while others are more suitable for the in vivo methods provided herein.

Some cadherin-11 antagonists bind to the extracellular domain of cadherin-11, some bind to particular regions of the extracellular domain of cadherin-11. As discussed herein, the cadherin-11 extracellular domain is comprised of five (5) subdomains each approximately about 110 amino acids in size. (See, for example, U.S. Pat. No. 7,589,074 and Yagi et al. Genes and Development, 14:1169-1180, 2000.) The invention contemplates the use of cadherin-11 antagonists that bind to cadherin-11 EC1 or to a fragment of cadherin-11 EC1 (e.g., a fragment that comprises about the first 33 through to the first 37 amino acids of EC1), or to a fragment of cadherin-11 that comprises EC1 (or the first 33-37 amino acids of EC1). In some embodiments, the antagonist binds to a region of EC1 having an amino acid sequence of GWVWN QFFVI EEYTG PDPVL VGRLH SDIDS GDGN (SEQ ID NO:3, the first 34 amino acids of EC1). Alternatively or additionally, the antagonist may comprise some or all of this amino acid sequence.

The cadherin-11 antagonist may be a peptide or protein, or it may be a nucleic acid, or it may be a organic or inorganic small molecule. The antagonists may be naturally occurring or non-naturally occurring. They may be isolated from a naturally occurring source or they may be synthesized in vitro.

The cadherin-11 antagonists may be conjugated to another agent such as an imaging agent or a cytotoxic agent. Imaging agents may be used to visualize cadherin-11 expression in vitro (e.g., for immunohistochemical analysis) or in vivo (e.g., for body imaging). Examples include radionuclides, contrast agents, and particulates routinely used in medical imaging. Cytotoxic agents are agents that are toxic to cells. Examples include chemotherapeutic agents, toxins, and the like. The use of these agents conjugated to a cadherin-11 antagonist will target such agents to fibrotic tissue and cells. In these instances, therapeutic benefit may be provided by a combination of the cadherin-11 antagonist which interferes with the ability of cadherin-11 to bind to a counter-receptor and the cytotoxic agent which is directly toxic to cells.

Cadherin-11 Binding Peptides:

Cadherin-11 antagonists that are peptide or protein in nature include (1) a full length cadherin-11 protein, (2) a fragment of the full length protein, wherein the fragment comprises the transmembrane domain of cadherin-11 or a fragment of the extracellular domain including for example a fragment comprising or consisting of EC1 (e.g., a fragment that comprises EC1, a fragment that comprises EC1 and EC2, a fragment that comprises EC1-EC3, a fragment that comprises EC1-EC4, a fragment that comprises EC1-EC5, a fragment that comprises EC1 and EC3, a fragment that comprises EC1 and EC4, a fragment that comprises EC1 and EC5), (3) a fragment of the full length protein, wherein the fragment comprises one or more of cadherin-11 extracellular subdomains (e.g., EC1, EC2, EC3, EC4, or EC5 of the 5 extracellular subdomains of cadherin-11, or any combination thereof), (4) fusion proteins that comprise full length cadherin-11 or a fragment thereof, and (5) antibodies and fragments thereof. In important embodiments, the cadherin-11 antagonist binds to and/or comprises the EC1 domain of cadherin-11 or a fragment thereof (such as SEQ ID NO:3 provided herein). Cadherin-11 antagonists that are peptide or protein in nature preferably will bind preferentially (or selectively) to cadherin-11. Preferential (or selective) binding to cadherin-11 means that the peptide or protein binds with greater affinity to cadherin-11 than to another protein. In some instances, the peptide or protein binds to cadherin-11 with an affinity that is about 2-fold more, about 3-fold more, about 4-fold more, about 5-fold more, about 10-fold more, about 25-fold more, about 50-fold more, about 100-fold more, about 1000-fold more, or more than its affinity for a protein that is not cadherin-11 or for any other moiety. Such differences in affinity are preferably manifest under physiological conditions as occur in vivo. In some embodiments, the cadherin-11 binding peptides bind to EC1 of cadherin-11, and optionally to the first 33-37 amino acids, including the first 33, first 34, first 35, first 36, or first 37 amino acids of EC1 of cadherin-11, as shown in SEQ ID NO:2 provided herein. Binding to this region of cadherin-11 can be determined through competitive binding assays using other binding agents known to bind to this region of cadherin-11 such as those described in WO2009/089062. The afore-mentioned antagonists are collectively referred to as cadherin-11 binding peptides. Cadherin-11 binding peptides may be harvested and isolated from naturally occurring sources or they may be synthesized and screened for their ability to bind to cadherin-11.

As used herein with respect to peptides and proteins, the term "isolated" means separated from its native environment in sufficiently pure form so that it can be manipulated or used for any one of the purposes of the invention.

Binding peptides can also be derived from sources other than antibody technology. For example, binding peptides can be provided by degenerate peptide libraries which can be readily prepared in solution, in immobilized form, as bacterial flagella peptide display libraries or as phage display libraries. Combinatorial libraries also can be synthesized of peptides containing one or more amino acids. Libraries can also be made that are comprised of peptides and non-peptide synthetic moieties.

Cadherin-11, or a fragment thereof, also can be used to isolate other cadherin-11 binding peptides or partners. Isolation of binding partners may be performed according to well-known methods. For example, cadherin-11 or a fragment thereof (e.g., an extracellular fragment) can be attached to a substrate, and then a putative cadherin-11 binding peptide may be applied to the substrate. If a cadherin-11 binding peptide is present, it will bind to the substrate-bound cadherin-11, and it can then be isolated and further analyzed.

Full-Length Cadherin-11 and Cadherin-11 Fragments:

Based on the known nucleotide and amino acid sequence of cadherin-11, suitable fragments of cadherin-11 may be identified and generated using conventional technology. Reference may be made to U.S. Pat. Nos. 5,597,725, 5,639,634, 5,646,250, 6,787,136, 6,946,768, 7,488,478, and 7589074, and PCT Patent Publication Nos. WO 93/21302 and WO2009/089062, the teachings of which relating to cadherin-11 nucleotide and amino acid sequences and fragments are incorporated by reference herein.

Examples of suitable fragments include those that consist of or comprise amino acids 1-40, 1-39, 1-38, 1-37, 1-36, 1-35, 1-34, 1-33, 1-32, 1-31 or 1-30 of cadherin EC1 or those that consist of or comprise amino acids 15-34, 15-35, 15-36, 15-37, 15-38, 15-39, or 15-40 of cadherin EC1. The first 40 amino acids of EC1 are underlined and the first 35 amino acids of EC1 are bolded in SEQ ID NO:2 as provided herein. Examples of suitable fragments are also provided in WO2009/089062 (represented by the amino acid sequences of SEQ ID NOs: 3, 10, 12, and 13, and also described in US 2009/0253200), the sequences of which are incorporated by reference herein. Other fragments may comprise amino acids 1-160, or 1-259, or 1-269 of SEQ ID NO:2, and optionally they may lack amino acids 1-53 of SEQ ID NO:2 which represents the leader and pro-region of human cadherin-11.

Cadherin-11 binding peptides may also be variants of full-length cadherin-11 or cadherin-11 fragments. Such variants may differ from cadherin-11 amino acid sequence by a degree. For example, variants may be about 80%, about 85%, about 90%, about 91%, about 92%, about 93%, about 94%, about 95%, about 96%, about 97%, about 98%, or about 99% identical to full length cadherin-11 or to a cadherin-11 fragment. Variants may comprise a cadherin-11 fragment and additional flanking constituents at the amino and/or carboxy end of the fragment. Such constituents may be amino acid in nature. In all instances, the variants bind to cadherin-11 and interfere with cadherin-11 function or activity.

Cadherin-11 binding peptides may be at least 10, 20, 30, 40, 50, 60, 70, 80, 90, 100, 110, amino acids in length or longer. For example, they may be about or at least 220, 330, 440, 550 amino acids in length.

In some important embodiments, the cadherin-11 inhibitory agent is a functionally equivalent peptide analog of cadherin-11. As used herein, the term functionally equivalent peptide analog refers to a peptide analog that is capable of inhibiting the binding of cadherin-11 to, for example, itself. Functionally equivalent peptide analogs of cadherin-11 are identified, for example, using in vitro adhesion assays that measure the ability of the peptide analog to inhibit cadherin-11-mediated adhesion either between cells expressing cadherin-11 or between isolated cadherin-11 proteins, or some combination thereof. Accordingly, exemplary functionally equivalent peptide analogs of cadherin-11 include analogs of full length cadherin-11 or a cadherin-11 fragment that for example comprises conservative amino acid substitutions relative to the wild-type sequence.

Still other cadherin-11 binding peptides are provided in PCT Published Application Nos. WO99/57149, WO2004/048411, and WO2009/089062, the specific teachings of which relating to cadherin-11 binding peptides and antagonists are incorporated by reference herein.

Cadherin-11 Fusion Proteins:

The cadherin-11 binding peptide can be a fusion protein. A fusion protein, as used herein, is a protein that contains peptide regions from at least two different proteins. For example, a cadherin-11 fusion protein contains amino acid sequence from cadherin-11 and at least one non-cadherin-11 protein. Such fusion proteins can be formed by fusing, usually at the nucleotide level, coding sequence from cadherin-11 to coding sequence from a non-cadherin-11 protein. Examples of cadherin-11 fusion proteins include cadherin-11 GST fusion protein, cadherin-11 Fc fusion protein, cadherin-11 beta-galactosidase fusion protein, cadherin-11 poly-His fusion protein, and cadherin-11 GFP fusion protein. Fc fusion proteins may comprise regions of the Ig constant domain, including without limitation the hinge region, the CH1 domain, the CH2 domain, and/or CH3 domain, optionally conjugated to the cadherin-11 fragment via the hinge domain. The Fc portion may derive from human antibodies or non-human antibodies. The antibodies may be IgG1 or IgG2, although they are not so limited. Methods of making Fc fusion proteins are known in the art and are described at least in EP0464533.

In some embodiments, the cadherin-11 fusion proteins comprise the entire extracellular domain of cadherin-11. In some embodiments, the cadherin-11 fusion protein comprises one or more extracellular subdomains of cadherin-11, such as EC1. Examples include fusion proteins comprising EC1, EC1/2, EC1-3, EC1-4, EC1/3, EC1/4, and EC1/5, or fragments of EC1. In important embodiments, the fusion protein binds to the EC1 domain of cadherin-11. Examples of cadherin-11 fusion proteins include cadherin-11-EC1-Fc fusion protein (comprising the EC1 domain of cadherin-11), cadherin-11-EC1/2-Fc fusion protein (comprising the EC1 and EC2 domains of cadherin-11), and cadherin-11-EC1-5-Fc fusion protein (comprising the EC1, EC2, EC3, EC4, and EC5 domains of cadherin-11). Some fusion proteins may comprise the first 40, first 39, first 38, first 37, first 36, first 35, or first 34 amino acids of the EC1 domain of cadherin-11, as described in WO 2009/089062.

Methods of synthesis of cadherin-11 fusion proteins can be found at least in U.S. Pat. Nos. 5,597,725, 5,639,634, 5,646,250, 6,787,136, 6,946,768, 7,488,478, and 7589074 and PCT Patent Publication No. WO 93/21302 and WO2009/089062 (see for example SEQ ID NOs: 6 and 7, the nucleotide and amino acid sequences of a human cadherin-11-EC1-hIgG2-

Fc fusion protein), the teachings of which relating to cadherin-11 fusion proteins are incorporated by reference herein.

Cadherin-11 Antibodies and Antibody Fragments:

Cadherin-11 antagonists that are cadherin-11 binding peptides may be antibodies or antigen-binding antibody fragments. The antibodies may be monoclonal antibodies or polyclonal antibodies. They may be chimeric antibodies including humanized antibodies. They may be four chain antibodies comprised of two heavy and two light chains, or they may be two chain antibodies such as those comprised of two heavy chains (such as camelid antibodies) or those comprised of a single heavy chain linked to a single light chain (such as a single chain Fvs). They can be of any type (e.g., IgG, IgE, IgM, IgD, IgA and IgY), class (e.g., IgG1, IgG2, IgG3, IgG4, IgA1 and IgA2) or subclass. As discussed below, these various antibody forms can be prepared according to conventional methodology. The antibodies and antibody fragments may be naturally occurring or non-naturally occurring including for example recombinantly produced antibodies and fragments.

Significantly, as is well-known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, I. (1991) *Essential Immunology*, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an F(ab')$_2$ fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

The terms Fab, Fab', Fc, Fd, pFc', F(ab')$_2$, Fv, and dAb are employed with either standard immunological meanings [Klein, Immunology (John Wiley, New York, N.Y., 1982); Clark, W. R. (1986) *The Experimental Foundations of Modern Immunology* (Wiley & Sons, Inc., New York); Roitt, I. (1991) *Essential Immunology*, 7th Ed., (Blackwell Scientific Publications, Oxford)]. Well-known functionally active antibody fragments include but are not limited to F(ab')$_2$, Fab, Fv and Fd fragments of antibodies. These fragments which lack the Fc fragment of intact antibody, clear more rapidly from the circulation, and may have less non-specific tissue binding than an intact antibody (Wahl et al., *J. Nucl. Med.* 24:316-325 (1983)). For example, single-chain antibodies can be constructed in accordance with the methods described in U.S. Pat. No. 4,946,778 to Ladner et al. Such single-chain antibodies include the variable regions of the light and heavy chains joined by a flexible linker moiety. Methods for obtaining a single domain antibody ("Fd") which comprises an isolated variable heavy chain single domain, also have been reported (see, for example, Ward et al., *Nature* 341:644-646 (1989), disclosing a method of screening to identify an antibody heavy chain variable region (V$_H$ single domain antibody) with sufficient affinity for its target epitope to bind thereto in isolated form). Methods for making recombinant Fv fragments based on known antibody heavy chain and light chain variable region sequences are known in the art and have been described, e.g., Moore et al., U.S. Pat. No. 4,462,334. Other references describing the use and generation of antibody fragments include e.g., Fab fragments (Tijssen, Practice and Theory of Enzyme Immunoassays (Elsevieer, Amsterdam, 1985)), Fv fragments (Hochman et al., Biochemistry 12: 1130 (1973); Sharon et al., Biochemistry 15: 1591 (1976); Ehrilch et al., U.S. Pat. No. 4,355,023) and portions of antibody molecules (Audilore-Hargreaves, U.S. Pat. No. 4,470, 925). Thus, those skilled in the art may construct antibody fragments from various portions of intact antibodies without destroying the specificity of the antibodies.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is now well-established in the art that the non-CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. Thus, for example, PCT International Publication No. WO 92/04381 and published European Patent Application No. EP 0239400 teach the production and use of humanized murine antibodies in which at least a portion of the murine FR regions have been replaced by FR regions of human origin. Such antibodies, including fragments of intact antibodies with antigen-binding ability, are often referred to as "chimeric" antibodies. There are entities in the United States which will synthesize humanized antibodies from specific murine antibody regions commercially, such as Protein Design Labs (Mountain View Calif.), Abgenix, and Medarex.

Thus, as will be apparent to one of ordinary skill in the art, the present invention also provides for F(ab')$_2$, Fab, Fv and Fd fragments; chimeric antibodies in which the Fc and/or FR and/or CDR1 and/or CDR2 and/or light chain CDR3 regions have been replaced by homologous human or non-human sequences; chimeric F(ab')$_2$ fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes single chain antibodies.

In addition, human monoclonal antibodies may be made by any of the methods known in the art, such as those disclosed in U.S. Pat. No. 5,567,610, issued to Borrebaeck et al., U.S. Pat. No. 565,354, issued to Ostberg, U.S. Pat. No. 5,571,893, issued to Baker et al, Kozber, *J. Immunol.* 133: 3001 (1984), Brodeur, et al., *Monoclonal Antibody Production Techniques and Applications*, p. 51-63 (Marcel Dekker, Inc, new York, 1987), and Boerner et al., *J. Immunol.,* 147: 86-95 (1991). In addition to the conventional methods for preparing human monoclonal antibodies, such antibodies may also be prepared by immunizing transgenic animals that are capable of producing human antibodies (e.g., Jakobovits et al., *PNAS USA,* 90: 2551 (1993), Jakobovits et al., *Nature,* 362: 255-258 (1993), Bruggermann et al., *Year in Immunol.,* 7:33 (1993) and U.S. Pat. No. 5,569,825 issued to Lonberg).

Exemplary cadherin-11 antibodies and methods for making such antibodies are described in U.S. Pat. Nos. 5,597,725, 5,639,634, 5,646,250, 6,787,136, 6,946,768, 7,488,478, and 7589074, and PCT Patent Publication No. WO 93/21302 and WO2009/089062, the teachings of which relating to cadherin-11 antibodies are incorporated by reference herein. Examples of cadherin-11 antibodies include 23C6, 13C2, 27F3, 5F82 (commercially available from Lifespan Science), H1M1 antibody (cadherin-11 EC1 specific antibody produced by hybridoma H1M1 having ATCC Accession No. PTA-9699), H14 antibody (cadherin-11 EC1 specific antibody produced by hybridoma H14 having ATCC Accession No. PTA-9701), BM5096/1A6 (commercially available from Acris Antibodies GmbH), 283416 (commercially available from R&D Systems), and MAB2014 (commercially available from Millipore). Examples of cadherin-11 antibody fragments include the Fab fragment of antibodies 23C6, 13C2, 27F3, 5F82, H1M1 antibody, H14 antibody, BM5096/1A6, 283416, and MAB2014. The antibodies or antibody fragments may comprise one or more CDRs from known antibodies such as the H1M1 or H14 antibodies, as described in US 2009/0253200, the CDR disclosure of which is incorporated by reference herein.

Antibodies and antibody fragments that bind to the EC1 domain of cadherin-11 are described in US 2009/0253200 and WO2009/089062 and such disclosures are incorporated by reference herein.

Cadherin-11 antibodies may also be bispecific or bifunctional antibodies capable of binding to two different epitopes by virtue of their different antigen-binding sites.

Still other cadherin-11 antibodies are camelid antibodies as described in PCT Publication No. WO 94/04678 and U.S. Patent Publication No. 20080124324, and their derivatives in the form of camelid nanobodies as in U.S. Pat. No. 5,759,808. Camelid antibodies and camelid nanobodies are commercially available from sources such as Ablynx (Belgium). It is to be understood that the cadherin-11 camelid antibodies can be humanized in a manner similar to that described herein for other antibody types.

Cadherin-11 Nucleic Acid Antagonists:

A cadherin-11 antagonist may also be a nucleic acid. These antagonists include nucleic acids that (1) encode a cadherin-11 polypeptide or a fragment thereof; (2) are cadherin-11 antisense molecules which inhibit the transcription or translation of the foregoing nucleic acid molecules; (3) are cadherin-11 inhibitory RNA (RNAi or siRNA); (4) are cadherin-11 ribozymes; (5) aptamers that are nucleic acid in nature but bind to the cadherin-11 as would binding peptides thereby interfering with the binding of cadherin-11 to another cadherin-11 or to another cadherin-11 counter-receptor. In some embodiments, a cadherin-11 antagonist that is a nucleic acid (1) hybridizes under stringent conditions to a nucleic acid having a sequence of SEQ ID NO: 1, and (2) codes for a cadherin-11 polypeptide or a fragment thereof that is capable of binding specifically to cadherin-11.

Cadherin-11 Encoding Nucleic Acids:

Cadherin-11 antagonists include nucleic acids that encode cadherin-11 and fragments of cadherin-11. The cadherin-11 full length nucleotide sequence is provided as SEQ ID NO:1.

Nucleic acids comprising a nucleotide sequence of SEQ ID NO:1 may be used as antagonists, as an example. The cadherin-11 antagonists of the invention also include homologs and alleles of a nucleic acid molecule comprising a sequence of SEQ ID NO: 1.

The cadherin-11 nucleic acid antagonists, may encode polypeptides which are soluble cadherin-11 polypeptides, membrane-bound polypeptides, or cadherin-11 fragments such as fragments that consist of or comprise EC1 or a fragment thereof (e.g., the first 33-37 amino acids of EC1). The soluble cadherin-11 polypeptides lack a transmembrane domain and, optimally, contain further amino acids which render the polypeptide soluble (e.g., fusion proteins, containing all or part of cadherin-11, which inhibit the binding of cadherin-11 to another cadherin-11). Cadherin-11 fragments which are membrane-bound (or membrane associated) preferably contain a transmembrane domain. Cadherin-11 nucleic acid antagonists further embrace nucleic acid molecules which code for a cadherin-11 protein having the amino acid sequence of SEQ ID NO: 2 (or SEQ ID NO:3, for example), but which may differ from the sequence of SEQ ID NO: 1 due to the degeneracy of the genetic code.

Certain cadherin-11 nucleic acid antagonists can be identified by conventional techniques, e.g., by identifying nucleic acid sequences which code for cadherin-11 and which hybridize to a nucleic acid molecule having the sequence of SEQ ID NO: 1 under stringent conditions. The term "stringent conditions," as used herein, refers to parameters with which the art is familiar. More specifically, stringent conditions, as used herein, refer to hybridization at 65 C in hybridization buffer (3.5×SSC, 0.02% formamide, 0.02% polyvinyl pyrolidone, 0.02% bovine serum albumin, 2.5 mM $NaH_2PO_4$ (pH 7), 0.5% SDS, 2 mM EDTA). SSC is 0.15 M sodium chloride/0.15 M sodium citrate, pH 7; SDS is sodium dodecyl sulphate; and EDTA is ethylenediaminetetraacetic acid. After hybridization, the membrane to which the DNA is transferred is washed at 2×SSC at room temperature and then at 0.1× SSC/0.1×SDS at 65 C.

There are other conditions, reagents, and so forth which can be used, which result in a similar degree of stringency. The skilled artisan will be familiar with such conditions and, thus, they are not given here. It will be understood, however, that the skilled artisan will be able to manipulate the conditions in a manner to permit the clear identification of homologs and alleles of the nucleic acid molecules of the invention. The skilled artisan also is familiar with the methodology for screening cells and libraries for the expression of further nucleic acids molecules which can be isolated and sequenced. In screening for cadherin-11 sequences for example, a Southern blot may be performed using the foregoing conditions, together with a radioactive probe. After washing the membrane to which the DNA is finally transferred, the membrane can be placed against x-ray film to detect the radioactive signal.

In general, cadherin-11 homologs and alleles typically will share at least 70% nucleotide identity with SEQ. ID. NO: 1; and in some instances, will share at least 75% nucleotide identity; and in still other instances, will share at least 80% nucleotide identity. Watson-Crick complements of the foregoing nucleic acids are also embraced by the invention. The preferred cadherin-11 homologs have at least 85% sequence homology to SEQ. ID. NO: 1. More preferably the cadherin-11 homologs have at least 90% and most preferably at least 95% sequence homology to SEQ. ID. NO: 1. The homology can be calculated using various, publicly available software tools developed by NCBI (Bethesda, Md.) that can be obtained through the internet. Exemplary tools include the BLAST system available at the NCBI website. Pairwise and ClustalW alignments (BLOSUM30 matrix setting) as well as Kyte-Doolittle hydropathic analysis can be obtained using the MacVector sequence analysis software (Oxford Molecular Group).

The invention also includes degenerate nucleic acids which include alternative codons to those present in the naturally occurring nucleic acid that encodes, for example, the human cadherin-11 polypeptide. As is well known in the art, and as an example, serine residues are encoded by the codons TCA, AGT, TCC, TCG, TCT and AGC. Each of the six codons is equivalent for the purposes of encoding a serine residue. Thus, it will be apparent to one of ordinary skill in the art that any of the serine-encoding nucleotide codons may be employed to direct the protein synthesis apparatus, in vitro or in vivo, to incorporate a serine residue. Similarly, nucleotide sequence triplets which encode other amino acid residues include, but are not limited to, CCA, CCC, CCG and CCT (proline codons); CGA, CGC, CGG, CGT, AGA and AGG (arginine codons); ACA, ACC, ACG and ACT (threonine codons); AAC and AAT (asparagine codons); and ATA, ATC and ATT (isoleucine codons). Other amino acid residues may be encoded similarly by multiple nucleotide sequences.

As used herein with respect to nucleic acids, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art.

The cadherin-11 nucleic acid antagonist, in one embodiment, is operably linked to a gene expression sequence which directs the expression of the cadherin-11 nucleic acid antagonist within a cell such as a eukaryotic cell. The "gene expression sequence" is any regulatory nucleotide sequence, such as a promoter sequence or promoter-enhancer combination which facilitates the efficient transcription and translation of the cadherin-11 nucleic acid antagonist to which it is operably linked. The gene expression sequence may, for example, be a mammalian or viral promoter, such as a constitutive or inducible promoter. Constitutive mammalian promoters include, but are not limited to, the promoters for the following genes: hypoxanthine phosphoribosyl transferase (HPTR), adenosine deaminase, pyruvate kinase, beta-actin promoter and other constitutive promoters. Exemplary viral promoters which function constitutively in eukaryotic cells include, for example, promoters from the simian virus, papilloma virus, adenovirus, human immunodeficiency virus (HIV), Rous sarcoma virus, cytomegalovirus, the long terminal repeats (LTR) of moloney leukemia virus and other retroviruses, and the thymidine kinase promoter of herpes simplex virus. Other constitutive promoters are known to those of ordinary skill in the art. The promoters useful as gene expression sequences of the invention also include inducible promoters. Inducible promoters are expressed in the presence of an inducing agent. For example, the metallothionein promoter is induced to promote transcription and translation in the presence of certain metal ions. Other inducible promoters are known to those of ordinary skill in the art.

In general, the gene expression sequence shall include, as necessary, 5' non-transcribing and 5' non-translating sequences involved with the initiation of transcription and translation, respectively, such as a TATA box, capping sequence, CAAT sequence, and the like. Especially, such 5' non-transcribing sequences will include a promoter region which includes a promoter sequence for transcriptional control of the operably joined cadherin-11 nucleic acid antagonist. The gene expression sequences optionally includes enhancer sequences or upstream activator sequences as desired.

Cadherin-11 nucleic acid antagonist may be used in both in vivo and in vitro methods. Nucleic acid molecules of the invention may be introduced into a cell in vitro, followed by the transfer of the cell to the site of fibrosis. The cell into which the nucleic acid molecule is introduced may be harvested from the site of fibrosis (e.g., a fibroblast) or it may be a cell which is not normally present at the site of inflammation. A sequence which permits expression of the nucleic acid in a particular tissue (or cell), such as for example the lung, is one which is selectively transcriptionally active in the tissue (or cell) and thereby causes the expression of the nucleic acid in the tissue (or cell). Those of ordinary skill in the art will be able to easily identify alternative promoters that are capable of expressing such a nucleic acid molecule in lung tissue, liver tissue, renal tissue, and the like, as mentioned herein. Alternatively, a cell transduced with the cadherin-11 nucleic acid antagonist may be cultured in vitro in order to produce a cadherin-11 protein antagonist or it may be used in in vitro screening assays. For example, the gene expression sequence may be used to express cadherin-11 in a cell which does not inherently express cadherin-11.

The nucleic acid molecule sequences of the invention and the gene expression sequence are said to be "operably linked" when they are covalently linked in such a way as to place the transcription and/or translation of the nucleic acid antagonist (e.g., a cadherin-11 coding sequence) under the influence or control of the gene expression sequence. If it is desired that nucleic acid molecule be translated into a functional protein, two DNA sequences are said to be operably linked if induction of a promoter in the 5' gene expression sequence results in the transcription of the nucleic acid molecule and if the nature of the linkage between the two DNA sequences does not (1) result in the introduction of a frame-shift mutation, (2) interfere with the ability of the promoter region to direct the transcription of the nucleic acid molecule, or (3) interfere with the ability of the corresponding RNA transcript to be translated into a polypeptide. Thus, a gene expression sequence would be operably linked to a nucleic acid molecule if the gene expression sequence were capable of effecting transcription of that nucleic acid molecule such that the resulting transcript might be translated into the desired polypeptide.

Cadherin-11 siRNA:

The invention contemplates the use of RNA interference agents such as siRNA and shRNA as cadherin-11 antagonists. siRNA are RNA molecules capable of causing interference and thus post-transcriptional silencing of specific genes in cells, including mammalian cells. siRNA comprise a double stranded region that is typically about 5-50 base pairs, more typically 10-40 base pairs, and even more typically 15-30 base pairs in length. The siRNA may be 20-50, 25-50 or 30-40 base pairs in length. These siRNA may be digested by the RNase III Dicer to yield smaller siRNA in the range of 19-28 base pairs, including 19 base pairs, 21 base pairs, 23 base pairs, 25 base pairs, and 27 base pairs in length. It is known that siRNA in this size range can be incorporated into and acted upon by the enzyme complex called RNA-Induced Silencing Complex (RISC), with a net result of target RNA degradation and/or inhibition of any protein translation therefrom. In a similar manner, double-stranded RNAs with other regulatory functions such as microRNAs (miRNA) can also be used. Reference can be made to Bass, Nature 411: 428-29 (2001); Elbashir et al., Nature 411: 494-98 (2001); Fire et al., Nature 391: 806-11 (1998); WO 01/75164, and U.S. Pat. Nos. 6,506,559, 7,056,704, 7,078,196, 7,432,250, for greater detail on siRNA as well as methods of making siRNA. siRNA to cadherin-11 are commercially available from sources such as Dharmacon.

siRNA forms such as the R- and L-form will have overhangs on one or both ends. As discussed herein, an R-form siRNA has a 3' overhang on its antisense strand. It may be blunted on its other end and/or it may have a 3' overhang on its other end, including an overhang comprising DNA residues. Alternatively, an L-form siRNA has a 3' overhang on its sense strand. It may be blunted on its other end and/or it may have a 3' overhang on its other end, including an overhang comprising DNA residues.

siRNA may be comprised of ribonucleotides or a combination of ribonucleotides and deoxyribonucleotides, including in some instances modified versions of one or both. For example, ribonucleotides containing a non-naturally occurring base (instead of a naturally occurring base) such as uridines and/or cytidines modified at the 5-position, e.g. 5-(2-amino)propyl uridine, 5-bromo uridine, or adenosines and/or guanosines modified at the 8-position, e.g. 8-bromo guanosine, or deaza nucleotides, e.g. 7-deaza-adenosine, or O- and N-alkylated nucleotides, e.g. N6-methyl adenosine can be incorporated into the siRNA. As another example, sugar-modified ribonucleotides having a 2' OH-group replaced by a group selected from H, OR, R, halo, SH, SR, $NH_2$, NHR, $NR_2$ or CN, wherein R is $C_1$-$C_6$ alkyl, alkenyl or alkynyl and halo is F, Cl, Br or I. As yet another example, the backbone may be modified to comprise modified backbone linkages such as but not limited to phosphorothioates. The siRNA may comprise modifications at the base, sugar and/or backbone, including a variety of such modifications.

Thus, siRNA molecules can be provided as and/or derived from one or more forms including, e.g., as one or more isolated small-interfering RNA (siRNA) double stranded duplexes, as longer double-stranded RNA (dsRNA), or as siRNA or dsRNA transcribed from a transcriptional cassette in a DNA plasmid. The siRNA molecules may have overhangs (e.g., 3' or 5' overhangs as described in Elbashir et al., Genes Dev., 15:188 (2001) or Nykanen et al., Cell, 107:309 (2001)), or may lack overhangs (i.e., have blunt ends). The person of ordinary skill in the art will appreciate and understand how such starting sources may be modified in order to arrive at the R- and L-forms described herein.

siRNA are targeted to genes in vivo or in vitro if all or part of the nucleotide sequence of their duplex (or double stranded) is complementary to a nucleotide sequence of the targeted gene, such as cadherin-11. siRNA made be synthesized based upon known (or predicted) nucleotide sequences of nucleic acids that encode proteins or other gene products. The sequence may be complementary to a translated or untranslated sequence in the target. The degree of complementarity between the siRNA and the target may be 100% or less than 100%, provided that sufficient identity exists to a target to mediate target-specific silencing. The art is familiar with efficacious siRNA that are less than 100% complementary to their target.

The level of silencing or interference may be measured in any number of ways, including quantitation of mRNA species and/or protein species. In some instances, mRNA quantitation is preferred particularly where the protein is intracellular or otherwise difficult to observe and/or assay. mRNA levels may be measured using RT-PCR or RACE, as an example. Protein levels may be measured using immunohistochemical staining. mRNA or protein levels may be reduced by 10%, 20%, 30%, 40%, 50%, 60%, 70%, 80%, 90%, 95%, 99%, or even 100%. Depending on the application, partial reduction (i.e., less than 100% may be sufficient) as compared to the level in the absence of the exogenously applied siRNA. In some embodiments, the level is reduced by 80% or more than 80% as compared to a control that has not been exposed to exogenously applied siRNA.

Cadherin-11 Ribozymes:

A cadherin-11 ribozyme is an enzymatic RNA molecule capable of catalyzing the specific cleavage of cadherin-11 RNA. The cadherin-11 ribozyme binds to cadherin-11 RNA in a sequence specific manner (i.e., via sequence specific hybridization), and this is followed by endonucleolytic cleavage of the cadherin-11 RNA. Examples of ribozymes include engineered hairpin or hammerhead motif ribozymes. Ribozyme sequences complementary to a target such as cadherin-11 can be identified by scanning the target for ribozyme cleavage sites (e.g., GUA, GUU, and GUC), and then generating a sequence having about 15-20 ribonucleotides spanning the cleavage site.

Cadherin-11 Antisense:

The cadherin-11 nucleic acid antagonist may be an antisense molecule (or oligonucleotide). Antisense oligonucleotides that selectively bind to a nucleic acid molecule encoding a cadherin-11 polypeptide, or a fragment thereof, to decrease cadherin-11 activity or function are embraced by the present invention. As used herein, the term "antisense oligonucleotide" or "antisense" describes an oligonucleotide that is an oligoribonucleotide, oligodeoxyribonucleotide, modified oligoribonucleotide, or modified oligodeoxyribonucleotide which hybridizes under physiological conditions to DNA comprising a particular gene or to an mRNA transcript of that gene and, thereby, inhibits the transcription of that gene and/or the translation of that mRNA. The antisense molecules are designed so as to interfere with transcription or translation of a target gene upon hybridization with the target gene or transcript. Those skilled in the art will recognize that the exact length of the antisense oligonucleotide and its degree of complementarity with its target will depend upon the specific target selected, including the sequence of the target and the particular bases which comprise that sequence. It is preferred that the antisense oligonucleotide be constructed and arranged so as to bind selectively with the target under physiological conditions, i.e., to hybridize substantially more to the target sequence than to any other sequence in the target cell under physiological conditions. Based upon SEQ ID NO:1 or upon allelic or homologous genomic and/or cDNA sequences, one of skill in the art can easily choose and synthesize any of a number of appropriate antisense molecules for use in accordance with the present invention. In order to be sufficiently selective and potent for inhibition, such antisense oligonucleotides should comprise at least 10 and, more preferably, at least 15 consecutive bases which are complementary to the target, although in certain cases modified oligonucleotides as short as 7 bases in length have been used successfully as antisense oligonucleotides (Wagner et al., *Nat. Med.* 1(11):1116-1118, 1995). Most preferably, the antisense oligonucleotides comprise a complementary sequence of 20-30 bases.

Although oligonucleotides may be chosen which are antisense to any region of the gene or mRNA transcripts, in preferred embodiments the antisense oligonucleotides correspond to N-terminal or 5' upstream sites such as translation initiation, transcription initiation or promoter sites. In addition, 3'-untranslated regions may be targeted by antisense oligonucleotides. Targeting to mRNA splicing sites has also been used in the art but may be less preferred if alternative mRNA splicing occurs. In addition, the antisense is targeted, preferably, to sites in which mRNA secondary structure is not expected (see, e.g., Sainio et al., *Cell Mol. Neurobiol.* 14(5): 439-457, 1994) and at which proteins are not expected to bind. Finally, although SEQ ID NO:1 discloses a cDNA sequence, one of ordinary skill in the art may easily derive the genomic DNA corresponding to this sequence. Thus, the present invention also provides for antisense oligonucleotides which are complementary to the genomic DNA corresponding to SEQ ID NO:1. Similarly, antisense to allelic or homologous cadherin-11 or alternatively, cadherin-11 counter-receptor cDNAs and genomic DNAs are enabled without undue experimentation.

In one set of embodiments, the antisense oligonucleotides of the invention may be composed of "natural" deoxyribonucleotides, ribonucleotides, or any combination thereof. That is, the 5' end of one native nucleotide and the 3' end of another native nucleotide may be covalently linked, as in natural systems, via a phosphodiester internucleoside linkage. These oligonucleotides may be prepared by art recognized methods which may be carried out manually or by an automated synthesizer. They also may be produced recombinantly by vectors.

In preferred embodiments, however, the antisense oligonucleotides of the invention also may include "modified" oligonucleotides. That is, the oligonucleotides may be modified in a number of ways which do not prevent them from hybridizing to their target but which enhance their stability or targeting or which otherwise enhance their therapeutic effectiveness.

The term "modified oligonucleotide" as used herein describes an oligonucleotide in which (1) at least two of its nucleotides are covalently linked via a synthetic internucleoside linkage (i.e., a linkage other than a phosphodiester linkage between the 5' end of one nucleotide and the 3' end of another nucleotide) and/or (2) a chemical group not normally associated with nucleic acids has been covalently attached to the oligonucleotide. Preferred synthetic internucleoside linkages are phosphorothioates, alkylphosphonates, phosphorodithioates, phosphate esters, alkylphosphonothioates, phosphoramidates, carbamates, carbonates, phosphate triesters, acetamidates, carboxymethyl esters and peptides.

The term "modified oligonucleotide" also encompasses oligonucleotides with a covalently modified base and/or sugar. For example, modified oligonucleotides include oligonucleotides having backbone sugars which are covalently attached to low molecular weight organic groups other than a hydroxyl group at the 3' position and other than a phosphate group at the 5' position. Thus modified oligonucleotides may include a 2'-O-alkylated ribose group. In addition, modified oligonucleotides may include sugars such as arabinose instead of ribose.

Delivery of Cadherin-11 Antagonists:

Nucleic acid antagonists can be delivered to a subject alone or in association with a vector. In its broadest sense, a "vector" is any vehicle capable of facilitating: (1) delivery of a nucleic acid molecule to a target cell and/or (2) uptake of a nucleic acid molecule by a target cell. Preferably, the vectors transport the cadherin-11 nucleic acid antagonist into the target cell with reduced degradation relative to the extent of degradation that would result in the absence of the vector. Optionally, a "targeting ligand" can be attached to the vector to selectively deliver the vector to a cell which expresses on its surface the cognate receptor for the targeting ligand. Methodologies for targeting include conjugates, such as those described in U.S. Pat. No. 5,391,723. In some instances, the nucleic acid molecules of the invention are targeted for delivery to a fibrotic tissue such as an affected lung, liver, kidney, and the like.

In general, the vectors useful in the invention are divided into two classes: biological vectors and chemical/physical vectors. Biological vectors are useful for delivery/uptake of nucleic acids to/by a target cell. Biological vectors include, but are not limited to, plasmids, phagemids, viruses, other vehicles derived from viral or bacterial sources that have been manipulated by the insertion or incorporation of the nucleic acid sequences of the invention, and additional nucleic acid fragments (e.g., enhancers, promoters) which can be attached to the nucleic acid sequences of the invention. Viral vectors are a preferred type of biological vector and include, but are not limited to, nucleic acid sequences from the following viruses: adenovirus; adeno-associated virus; retrovirus, such as moloney murine leukemia virus; harvey murine sarcoma virus; murine mammary tumor virus; rouse sarcoma virus; SV40-type viruses; polyoma viruses; Epstein-Barr viruses; papilloma viruses; herpes virus; vaccinia virus; polio virus; and RNA virus such as a retrovirus. One can readily employ other vectors not named but known in the art.

A particularly preferred virus for certain applications is the adeno-associated virus, a double-stranded DNA virus. The adeno-associated virus is capable of infecting a wide range of cell types and species and can be engineered to be replication-deficient. It further has advantages, such as heat and lipid solvent stability, high transduction frequencies in cells of diverse lineages, including hemopoietic cells, and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

In general, other preferred viral vectors are based on non-cytopathic eukaryotic viruses in which non-essential genes have been replaced with the gene of interest. Non-cytopathic viruses include retroviruses, the life cycle of which involves reverse transcription of genomic viral RNA into DNA with subsequent proviral integration into host cellular DNA. Adenoviruses and retroviruses have been approved for human gene therapy trials. In general, the retroviruses are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell line with plasmid, production of recombinant retroviruses by the packaging cell line, collection of viral particles from tissue culture media, and infection of the target cells with viral particles) are provided in Kriegler, M., "Gene Transfer and Expression, A Laboratory Manual," W.H. Freeman C.O., New York (1990) and Murry, E. J. Ed. "Methods in Molecular Biology," vol. 7, Humana Press, Inc., Cliffton, N.J. (1991). Another preferred retroviral vector is the vector derived from the moloney murine leukemia virus, as described in Nabel, E. G., et al., *Science*, v. 249, p. 1285-1288 (1990).

In addition to the biological vectors, chemical/physical vectors are useful for delivery/uptake of nucleic acids or polypeptides to/by a target cell. As used herein, a "chemical/physical vector" refers to a natural or synthetic molecule, other than those derived from bacteriological or viral sources, capable of delivering the cadherin-11 antagonist to a cell.

A preferred chemical/physical vector of the invention is a colloidal dispersion system. Colloidal dispersion systems include lipid-based systems including oil-in-water emulsions, micelles, mixed micelles, and liposomes. A preferred colloidal system of the invention is a liposome. Liposomes are artificial membrane vessels which are useful as a delivery vector in vivo or in vitro. It has been shown that large unilamellar vessels (LUV), which range in size from 0.2-4.0 µM can encapsulate large macromolecules. RNA, DNA, and intact virions can be encapsulated within the aqueous interior and be delivered to cells in a biologically active form (Fraley, et al., *Trends Biochem. Sci.*, v. 6, p. 77 (1981)). In order for a liposome to be an efficient gene transfer vector, one or more of the following characteristics should be present: (1) encapsulation of the gene of interest at high efficiency with retention of biological activity; (2) preferential and substantial binding to a target cell in comparison to non-target cells; (3) delivery of the aqueous contents of the vesicle to the target cell cytoplasm at high efficiency; and (4) accurate and effective expression of genetic information.

Liposomes may be targeted to a particular tissue, by coupling the liposome to a specific ligand such as a monoclonal antibody, sugar, glycolipid, or protein specific for the particular tissue or cell type. Additionally, the vector may be coupled to a nuclear targeting peptide, which will direct the cadherin-11 modulating nucleic acid molecule to the nucleus of the host cell.

Liposomes are commercially available from Gibco BRL, for example, as LIPOFECTIN™ and LIPOFECTACE™, which are formed of cationic lipids such as N-[1-(2, 3 dioleyloxy)-propyl]-N,N,N-trimethylammonium chloride (DOTMA) and dimethyl dioctadecylammonium bromide (DDAB). Methods for making liposomes are well known in the art and have been described in many publications. Liposomes also have been reviewed by Gregoriadis, G. in *Trends in Biotechnology*, V. 3, p. 235-241 (1985).

In general, the cadherin-11 nucleic acid antagonists can be administered to the subject (any mammalian recipient) using the same modes of administration that currently are used for gene therapy in humans (e.g., adenovirus-mediated gene therapy). A patented procedure for performing ex vivo gene therapy is outlined in U.S. Pat. No. 5,399,346 and in exhibits submitted in the file history of that patent, all of which are publicly available documents. In general, ex vivo gene therapy involves introduction in vitro of a functional copy of a gene or fragment thereof into a cell(s) of a subject and returning the genetically engineered cell(s) to the subject. The functional copy of the gene or fragment thereof is under operable control of regulatory elements which permit expression of the gene in the genetically engineered cell(s). Numerous transfection and transduction techniques as well as appropriate expression vectors are well known to those of ordinary skill in the art, some of which are described in PCT application WO95/00654.

As an illustrative example, a vector containing a nucleic acid molecule is delivered to a site of fibrosis in a subject who is a candidate for such gene therapy. Then, the vector genetically modifies one or more cell types in the fibrotic environment with DNA encoding, for example, cadherin-11. Such genetically modified cells are expected to interfere with cadherin-11 binding to another cadherin-11.

In an alternative embodiment, primary human cells can be obtained from a subject who is a candidate for such gene therapy. Then, such cells can be genetically engineered ex vivo with DNA encoding, for example, a full length cadherin-11. Such recombinant cells are expected to inhibit cadherin-11 mediated adhesion in vivo. In yet another example, another cell type which does not express cadherin-11 can be genetically manipulated in vitro to express a cadherin-11 antagonist and then introduced into the site of fibrosis.

Exemplary compositions that can be used to facilitate in vitro uptake of nucleic acids by a target cell include calcium phosphate and other chemical mediators of intracellular transport, microinjection compositions, electroporation and homologous recombination compositions (e.g., for integrating a nucleic acid into a preselected location within the target cell chromosome).

Pharmaceutical Compositions, Formulations, Effective Amounts:

The invention further provides a pharmaceutical composition (i.e., a pharmaceutical preparation) comprising a cadherin-11 antagonist. The composition includes a pharmaceutically acceptable carrier and a cadherin-11 antagonist.

The pharmaceutical preparations, as described above, are administered in effective amounts. For therapeutic applications, it is generally that amount sufficient to achieve a medically desirable result. In general, a therapeutically effective amount is that amount necessary to delay the onset of, inhibit the progression of, or halt altogether the particular condition being treated. As an example, the effective amount may be that amount which serves to reduce, alleviate, or delay the onset of the symptoms (e.g., pain, inflammation, etc.) of the disorder being treated or prevented. The effective amount will depend upon the mode of administration, the particular condition being treated and the desired outcome. It will also depend upon the stage of the condition, the severity of the condition, the age and physical condition of the subject being treated, the nature of concurrent therapy, if any, the duration of the treatment, the specific route of administration and like factors within the knowledge and expertise of the medical practitioner. For prophylactic applications, it is that amount sufficient to delay the onset of, inhibit the progression of, or halt altogether the particular condition being prevented, and may be measured by the amount required to prevent the onset of symptoms.

Generally, doses of active compounds of the present invention would be from about 0.01 mg/kg per day to 1000 mg/kg per day, preferably from about 0.1 mg/kg to 200 mg/kg and most preferably from about 0.2 mg/kg to about 20 mg/kg, in one or more dose administrations daily, for one or more days. It is expected that doses ranging from 1-500 mg/kg, and preferably doses ranging from 1-100 mg/kg, and even more preferably doses ranging from 1-50 mg/kg, will be suitable. The preferred amount can be determined by one of ordinary skill in the art in accordance with standard practice for determining optimum dosage levels of the agent. It is generally preferred that a maximum dose of a cadherin-11 antagonist that is the highest safe dose according to sound medical judgment be used.

The cadherin-11 antagonists can be administered to a subject in need of such treatment in combination with concurrent therapy for treating fibrosis. The concurrent therapy may be invasive or non-invasive (e.g., drug therapy). Examples of drug therapies for fibrosis include but are not limited to methiazole, piperlongumine, antimycin a, thiostrepton, benzbromarone, luteolin, tolfenamic acid, ciclopirox ethanolamine, (r)-(−)-apomorphine calciferol, GBR 12909, harmol, hycanthone, flufenamic acid, halofantrine, and zardaverine, as described in U.S. Patent Publication No. 20100093613. Immunosuppressants have also been used in the treatment of fibrosis. Examples include rapamycin, methotrexate, azathioprine, cyclosporin, FK-506, CDK inhibitors, and steroids and corticosteroids such as cortisone, dexamethasone, hydrocortisone, methylprednisolone, prednisolone, prednisone, and triamcinoline Other agents that may be used include anti-inflammatory agents such as the NSAIDs. These drug therapies are well-known to those of ordinary skill in the art and are administered by modes known to those of such skill. The drug therapies are administered in amounts which are effective to achieve the physiological goals, in combination with cadherin-11 antagonists. Thus, it is contemplated that in some instances the drug therapies may be administered in amounts which are not capable of preventing or reducing the physiological consequences of fibrosis when the drug therapies are administered alone but which are capable of reducing the consequences when administered in combination with the cadherin-11 antagonists. The cadherin-11 antagonist may be formulated with such secondary therapeutic agents or they may be formulated separately. They may be administered at the same time or at separate times. For example, the cadherin-11 antagonist may be administered before, and/or with, and/or after the secondary therapeutic agent. Alternatively, the secondary therapeutic agent may be administered before, and/or with, and/or after the cadherin-11 antagonist.

The cadherin-11 antagonists may be administered alone or in combination with the above-described drug therapies as part of a pharmaceutical composition. Such a pharmaceutical composition may include the cadherin-11 antagonist in combination with any standard physiologically and/or pharmaceutically acceptable carriers which are known in the art. The compositions should be sterile and contain a therapeutically effective amount of the cadherin-11 modulating agent in a unit of weight or volume suitable for administration to a patient.

The term "pharmaceutically-acceptable carrier" as used herein means one or more compatible solid or liquid filler, diluents or encapsulating substances which are suitable for administration into a human or other animal. The term "pharmaceutically acceptable" means a non-toxic material that does not interfere with the effectiveness of the biological activity of the active ingredients. Pharmaceutically acceptable further means a non-toxic material that is compatible with a biological system such as a cell, cell culture, tissue, or organism. The term "carrier" denotes an organic or inorganic ingredient, natural or synthetic, with which the active ingredient is combined to facilitate the application. The characteristics of the carrier will depend on the route of administration. The components of the pharmaceutical compositions also are capable of being commingled with the agents of the present invention, and with each other, in a manner such that there is no interaction which would substantially impair the desired pharmaceutical efficacy. The pharmaceutically acceptable carrier must be sterile for in vivo administration. Physiologically and pharmaceutically acceptable carriers include diluents, fillers, salts, buffers, stabilizers, solubilizers, and other materials which are well known in the art.

Compositions suitable for parenteral administration conveniently comprise a sterile aqueous preparation of the cadherin-11 modulating agents, which is preferably isotonic with the blood of the recipient. This aqueous preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or di-glycerides. In addition, fatty acids such as oleic acid may be used in the preparation of injectables. Carrier formulations suitable for oral, subcutaneous, intravenous, intramuscular, etc. administrations can be found in Remington's Pharmaceutical Sciences, Mack Publishing Co., Easton, Pa.

A variety of administration routes are available. The particular mode selected will depend, of course, upon the particular non-dermal fibrosis being treated, the severity of the condition being treated, and the dosage required for therapeutic efficacy. The methods of the invention, generally speaking, may be practiced using any mode of administration that is medically acceptable, meaning any mode that produces effective levels of the active compounds without causing clinically unacceptable adverse effects. Such modes of administration include oral, rectal, topical, nasal, inhalation, or parenteral routes. The term "parenteral" includes subcutaneous, intravenous, intramuscular, intraperitoneal, or infusion.

The pharmaceutical compositions may conveniently be presented in unit dosage form and may be prepared by any of the methods well-known in the art of pharmacy. All methods include the step of bringing the cadherin-11 antagonists into association with a carrier which constitutes one or more accessory ingredients. In general, the compositions are prepared by uniformly and intimately bringing the cadherin-11 antagonists into association with a liquid carrier, a finely divided solid carrier, or both, and then, if necessary, shaping the product. Compositions suitable for oral administration may be presented as discrete units, such as capsules, tablets, lozenges, each containing a predetermined amount of the cadherin-11 antagonist. Other compositions include suspensions in aqueous liquids or non-aqueous liquids such as a syrup, elixir or an emulsion.

In one particular embodiment, the preferred vehicle for delivery of the cadherin-11 antagonists is a biocompatible microparticle or implant that is suitable for implantation into a subject. Exemplary bioerodible implants that are useful in accordance with this method are described in PCT International application no. PCT/US/03307 (Publication No. WO 95/24929, entitled "Polymeric Gene Delivery System", claiming priority to U.S. patent application Ser. No. 213,668, filed Mar. 15, 1994). PCT/US/0307 describes a biocompatible, preferably biodegradable polymeric matrix for containing an exogenous gene under the control of an appropriate promoter. The polymeric matrix is used to achieve sustained release of the exogenous gene in the subject. In accordance with the instant invention, the cadherin-11 modulating agents described herein are encapsulated or dispersed within the biocompatible, preferably biodegradable polymeric matrix disclosed in PCT/US/03307. The polymeric matrix preferably is in the form of a microparticle such as a microsphere (wherein, for example, the cadherin-11 inhibitory agent is dispersed throughout a solid polymeric matrix) or a microcapsule (wherein, for example, the cadherin-11 inhibitory agent is stored in the core of a polymeric shell). Other forms of the polymeric matrix for containing the cadherin-11 modulating agent include films, coatings, gels, implants, and stents. The size and composition of the polymeric matrix device is selected to result in favorable release kinetics in the tissue into which the matrix device is implanted. The size of the polymeric matrix devise is further selected according to the method of delivery which is to be used, including for example administration of a suspension by aerosol into the nasal and/or pulmonary areas. The polymeric matrix composition can be selected to have both favorable degradation rates and also to be formed of a material which is bioadhesive. The matrix composition also can be selected not to degrade, but rather, to release by diffusion over an extended period of time.

Both non-biodegradable and biodegradable polymeric matrices can be used to deliver the cadherin-11 antagonists to the subject. Biodegradable matrices are preferred. Such polymers may be natural or synthetic polymers. Synthetic polymers are preferred. The polymer is selected based on the period of time over which release is desired, generally in the order of a few hours to a year or longer. Typically, release over a period ranging from between a few hours and three to twelve months is most desirable. The polymer optionally is in the form of a hydrogel that can absorb up to about 90% of its weight in water and further, optionally is cross-linked with multivalent ions or other polymers.

In general, the cadherin-11 antagonists are delivered using the bioerodible implant by way of diffusion, or more preferably, by degradation of the polymeric matrix. Exemplary synthetic polymers which can be used to form the biodegradable delivery system include: polyamides, polycarbonates, polyalkylenes, polyalkylene glycols, polyalkylene oxides, polyalkylene terepthalates, polyvinyl alcohols, polyvinyl ethers, polyvinyl esters, poly-vinyl halides, polyvinylpyrrolidone, polyglycolides, polysiloxanes, polyurethanes and co-polymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), polyvinyl acetate, poly vinyl chloride, polystyrene and polyvinylpyrrolidone.

Examples of biodegradable polymers include synthetic polymers such as polymers of lactic acid and glycolic acid, polyanhydrides, poly(ortho)esters, polyurethanes, poly(butic acid), poly(valeric acid), and poly(lactide-co-caprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

Bioadhesive polymers of particular interest include bioerodible hydrogels (described by H. S. Sawhney, C. P. Pathak and J. A. Hubell in Macromolecules, 1993, 26, 581-587, the teachings of which are incorporated herein), polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

Examples of non-biodegradable polymers include ethylene vinyl acetate, poly(meth)acrylic acid, polyamides, copolymers and mixtures thereof.

Other delivery systems can include time-release, delayed release or sustained release delivery systems. Such systems can avoid repeated administrations of the cadherin-11 antagonists described above, increasing convenience to the subject and the physician. Many types of release delivery systems are available and known to those of ordinary skill in the art. They include the above-described polymeric systems, as well as polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono- di- and tri-glycerides; hydrogel release systems; silastic systems; peptide based systems; wax coatings; compressed tablets using conventional binders and excipients; partially fused implants; and the like. Specific examples include, but are not limited to: (a) erosional systems in which the cadherin-11 modulating agent is contained in a form within a matrix such as those described in U.S. Pat. Nos. 4,452,775, 4,675,189 and 5,736,152 and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

Use of a long-term sustained release implant may be particularly suitable for treatment of chronic conditions. Long-term release, are used herein, means that the implant is constructed and arranged to delivery therapeutic levels of the active ingredient for at least 30 days, and preferably 60 days. Long-term sustained release implants are well-known to those of ordinary skill in the art and include some of the release systems described above.

Detecting Cadherin-11 and Measuring Cadherin-11 Levels:

As discussed herein, the invention contemplates detecting cadherin-11 levels in tissues or cells of subjects in order to determine whether the subject has non-dermal fibrosis (resulting is a diagnosis of non-dermal fibrosis) or whether the subject is likely to develop non-dermal fibrosis (resulting in a prognosis of non-dermal fibrosis). Also as discussed above, diagnosis or prognosis may involve consideration of other factors such as contemporaneous symptoms of non-dermal fibrosis, familial history, or patient history (including information about etiological factors known to contribute or cause non-dermal fibrosis).

Detection of cadherin-11 levels may involve detecting cadherin-11 genomic DNA levels, mRNA levels, miRNA levels, and/or protein levels. Methods for detecting any of the foregoing are known in the art, and include PCR, RT-PCR, immunohistochemistry, FACS analysis, ELISA, Southern analysis, Northern analysis, Western analysis, microarray analysis, etc. Diagnosis and/or prognosis of non-dermal fibrosis may be indicated by the presence of cadherin-11 levels that are abnormally elevated in the tissue or cells of interest. Abnormally elevated levels are defined as levels that are higher than the level in a normal tissue (or a section of tissue) or cells that are non-fibrotic. Thus, in order to determine whether the level of cadherin-11 is abnormally elevated, it is typically compared to the level of cadherin-11 in a normal (non-fibrotic) tissue (or a non-fibrotic region of a tissue) or cells, or to a pre-determined normal level of cadherin-11. Pre-determined normal levels of cadherin-11 for a given tissue may be available based on population studies or other historical data. Accordingly, the comparison need not be made strictly to tissue or cells in the subject.

The cadherin-11 level in a subject is typically determined from a sample harvested from a subject. The nature of the sample will typically depend upon the type of non-dermal fibrosis. For example, if the non-dermal fibrosis is lung fibrosis, the sample may be, for example, a lung biopsy or resected lung tissue. In important embodiments, it may be a bronchoalveolar lavage (BAL) sample. The harvest of such samples is known in the art.

An abnormally elevated level of cadherin-11 may be a level that is about 5%, about 10%, about 20%, about 30%, about 40%, about 50%, about 60%, about 70%, about 80%, about 90%, or about 100% greater than the level in a normal control sample. The degree to which the cadherin-11 level is elevated may indicate the extent of disease, such that lower elevated levels may be indicative of disease onset while higher elevated levels may be indicative of establishment of the disease.

It is to be understood that the cadherin-11 antagonists described herein may be used for the purpose of detecting and measuring cadherin-11 levels, as will be readily apparent to those of ordinary skill in the art.

The following Examples are included for purposes of illustration and are not intended to limit the scope of the invention.

EXAMPLES

Example 1

To investigate whether cadherin-11 levels are upregulated during the process of lung fibrosis, the bleomycin-induced lung fibrosis model was used. Wild type mice (C57BL/6) were administered either saline (control) or bleomycin via the intratracheal route. Twelve days after the administration of bleomycin or saline, mice were humane sacrificed and lungs were processed for histology and western blot analyses to determine if cadherin-11 is increased during lung fibrosis in this mouse model. Protein lysates were separated on a 10% acrylamide gel by electrophoresis, then transfer to a membrane for western blotting using isotype control antibody, anti-cadherin-11 antibody (Invitrogen) or anti-GAPDH antibody. Wild type and cadherin-11 null fibroblast-like synoviocytes were used as positive and negative controls for the expression of cadherin-11. The bleomycin lung had increased levels of cadherin-11 but similar levels of GAPDH (FIG. 1). These data indicate that cadherin-11 is increased during the process of lung fibrosis.

Figure 2:
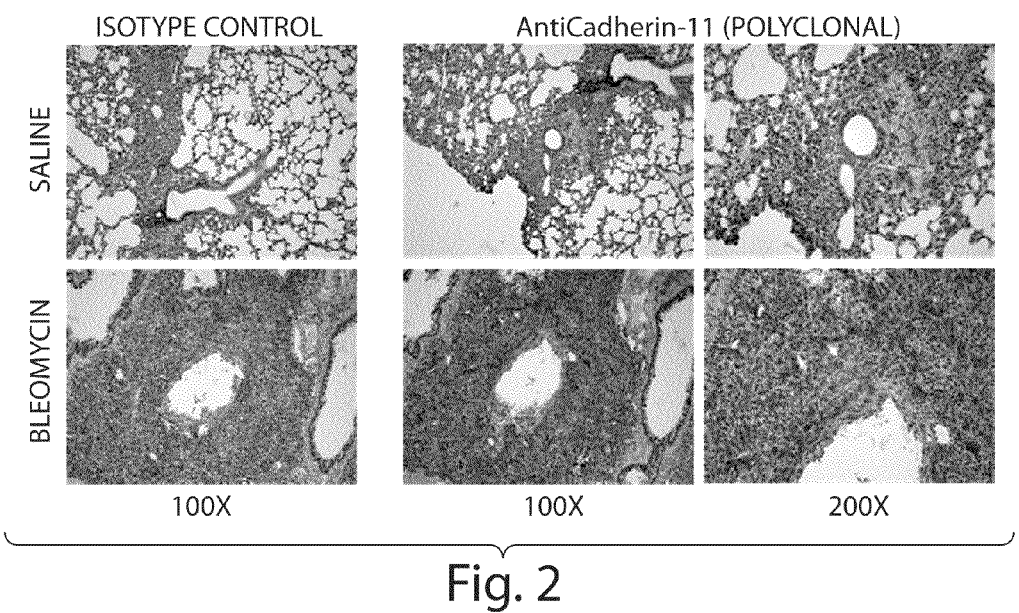
FIG. 2. Immunohistochemical analyses of lungs of wild type mice administered saline or bleomycin via the intratracheal route. Lungs were harvested on day 12. Lung sections from mice administered intratracheal bleomycin demonstrated prominent staining of cadherin-11 on fibroblast-like cells in the areas that are forming fibrotic foci (red stain).

To determine the cellular localization of cadherin-11 staining, tissue was processed for histological analyses and stained with rabbit polyclonal antibodies against cadherin-11 or isotype control. As seen in FIG. 2, lung sections from mice administered intratracheal bleomycin demonstrated prominent staining of cadherin-11 on fibroblast-like cells in the areas that are forming fibrotic foci (red stain). In saline administered lung sections, there is no staining of cadherin-11 within these areas.

Together these data demonstrate that cadherin-11 levels are increased early (day 12) in the fibrotic lungs in the bleomycin induced lung fibrosis model and strongly suggest that cadherin-11 may be involved in the development of fibrosis and serve as a therapeutic target.

Example 2

This Example demonstrates that cadherin-11 levels are increased in lungs from patients with idiopathic pulmonary fibrosis. Using mice that genetically lack cadherin-11 and mouse models of lung fibrosis, we also demonstrate that cadherin-11 is a critical mediator of fibrosis in the lung. These data indicate that cadherin-11 is a therapeutic target for pulmonary fibrosis.

Methods:

Human Subjects.

Surgical lung biopsy tissue samples were obtained from the Lung Tissue Research Consortium. Patients were classified as having mild IPF and severe IPF according to spirometry, pathological examination and high resolution CT scan. Bronchoalveolar lavage (BAL) fluid was obtained from discarded BAL obtained for routine clinical purposes in the evaluation of patients with IPF or fibrosing lung diseases. The studies were approved by the Committee for the Protection of Human Subjects at the University of Texas Health Science Center at Houston.

Mice.

Female mice aged 6-10 weeks were used for these studies. Cadherin-11 null mice and control B6:129 F1 intercross mice were maintained at in the animal care facility at the University of Texas Health Science Center at Houston.[17] C57BL/6 wild-type mice were raised at Jackson Laboratories (Bar Harbor, Me.). All animal protocols were approved by the University of Texas Health Science Center at Houston Animal Care and Use Committee.

Bleomycin Lung Fibrosis Model.

8-10 week old female mice were used for these experiments. Mice were anesthetized with avertin (250 mg/kg, intraperitoneally), and 3.5 U/kg bleomycin (Teva Parenteral Medicines, Irvine, Calif.) diluted in 50 µl sterile saline or saline alone was instilled intratracheally. On day 21, mice were humanely sacrificed and lungs harvested for analyses. Prior to harvesting the lungs, bronchoalveolar lavages were obtained with 3 lavages of 0.4 ml of PBS. Lungs were then infused with 10% buffered formalin at 25 cm of pressure and fixed overnight at 4° C.

Immunohistochemistry.

Tissue biopsies were processed for immunohistology. Five µm sections were deparaffinized, rehydrated, and immersed in TBS-T buffer (Tris-buffered saline and 0.1% Tween 20), and treated with target retrieval solution (DAKO, Carpinteria, Calif.) at 95° C. for 10 minutes. Rabbit polyclonal primary antibodies against cadherin-11 (Invitrogen Inc) or isotype matched control antibody (Abcam Inc., Cambridge, Mass.) were used. Bound antibodies were detected using secondary antibodies from the Dako Cytomation Envision System-HRP (3,3-diaminobenzidine tetrahydrochloride). Sections were counterstained with hematoxylin.

RNA Isolation and Quantitative Real Time PCR.

Tissue biopsies frozen in RNALater (Qiagen, Valencia, Calif.) were used for RNA isolation. RNA was isolated using the RNeasy Fibrous Tissue Mini Kit using the manufacturer's instructions (Qiagen, Valencia, Calif.). RNA concentration and purity was determined using the Nanodrop method. One microgram of total RNA was used to synthesize cDNA using Quantitect reverse transcription kits using the manufacturer's instructions (Qiagen, Valencia, Calif.). Quantitative real-time PCR (qRT-PCR) was performed using validated TaqMan Gene Expression Assays for specific genes of interest and normalized to cyclophilin (Applied Biosystems Inc) on an Applied Biosystems 7900HT Fast Real-Time PCR System (Applied Biosystems Inc). Cyclophilin was used as an endogenous control to normalize transcript levels of total RNA of each sample. The data were analyzed with SDS 2.3 software using the comparative CT method (2-ddCT method). Fold change was calculated as 2ddCT.

Cadherin-11 siRNA Knock-Down.

A549 cells (ATCC) were seeded in 96 well plates and grown overnight in DMEM containing 10% FBS and 1% antibiotics. For siRNA knockdown of Cdh11, cells were washed with antibiotic free media and subsequently incubated with Optimem (Invitrogen) with Lipofectamine RNAiMax (Invitrogen) and either non-targeting siRNA or human Cdh11 siRNA (antisense sequence: 5'-UUUGAAUG-GAGUCAUAAGGUU) (SEQ ID NO:4) (Dharmacon RNAi Technologies, Thermo) for 48 hours. Cells were then trypsinized and reseeded in antibiotic free medium. Six hours later, cells were serum-starved overnight in DMEM containing 0.1% BSA. Cells were then stimulated with or without TGF-β at 10 ng/ml in DMEM+0.1% BSA for 24 hours. RNA was isolated using Cell to Ct reagents (Ambion) according to manufacturer's instructions. Transcripts for CDH11, COL1A1, N cadherin (Cdh2), and E cadherin (Cdh1) were obtained with corresponding Taqman probes (Applied Biosystems) and presented as mean fold change versus control. Imaging of A549 cells was performed with a BX60 inverted phase contrast microscope (Olympus) for determination of cellular morphology.

Results:

Pulmonary Fibrosis.

Figure 3:
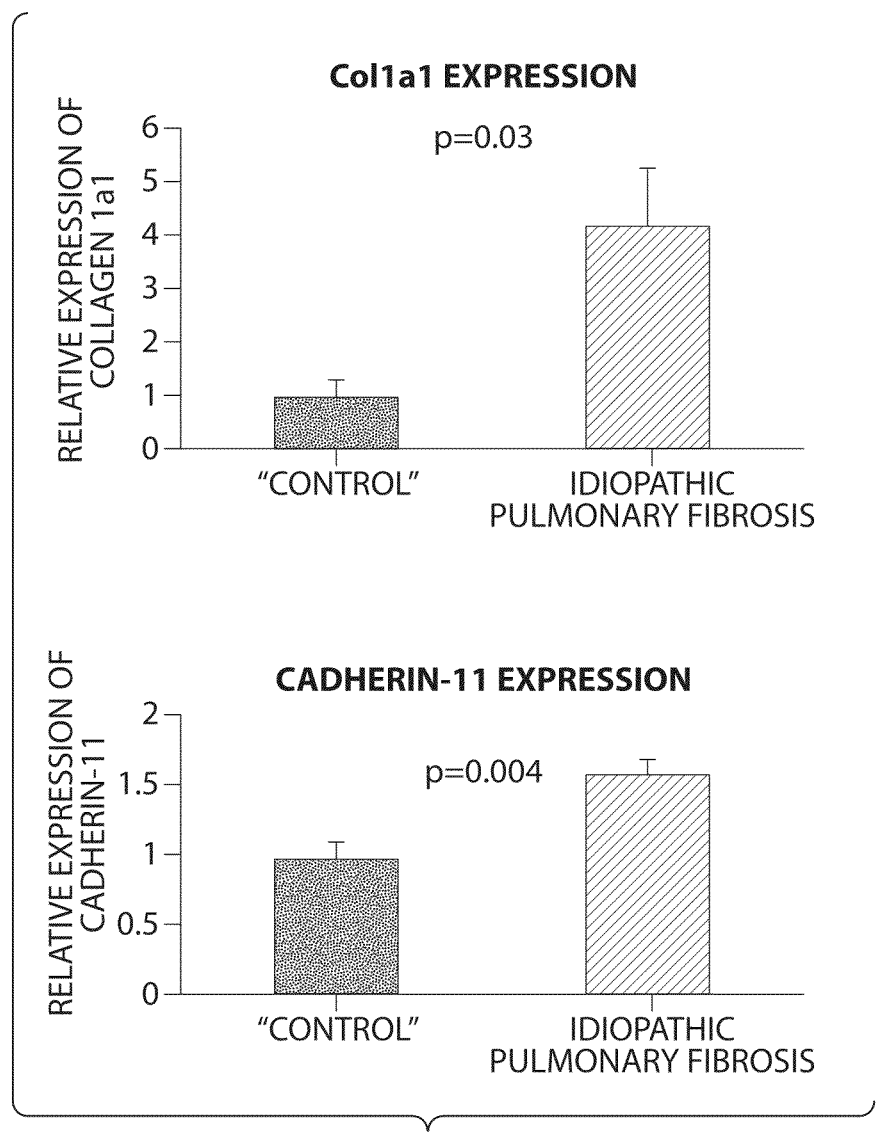
FIG. 3. mRNA levels of Col1a1 and cadherin-11 in lung tissue are increased in patients with severe IPF. Lung tissue was obtained from the Lung Tissue Research Consortium from 8 subjects with mild IPF and normal lung function (control, blue) and 10 subjects with severe IPF and abnormal lung function (IPF, red). Col1a1 was used as a control and was increased in patients with severe IPF. Cadherin-11 levels were also increased in patients with severe IPF. P-values determined using Student T-test.

Expression and localization of cadherin 11 in patients with interstitial lung disease. To determine if cadherin-11 expression is increased in lungs of patients with pulmonary fibrosis, cadherin-11 mRNA levels was assessed total RNA isolated from lungs of patients with idiopathic pulmonary fibrosis (IPF) with severe airway restriction versus IPF patients with normal lung function (mild IPF lungs were used as "control"). As seen in FIG. 3, lung tissue from severe IPF patients had increased levels of type I collagen (Col1a1), a major component of the fibrotic extracellular matrix. Consistent with our hypothesis, lung tissue from severe IPF patients had increased levels of cadherin-11.

Figure 4A:
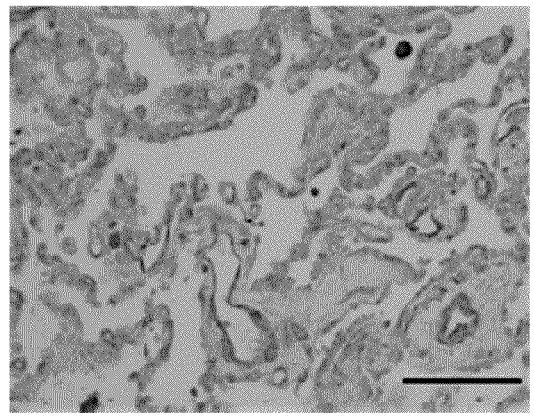
FIG. 4. Immunolocalization of cadherin-11 expression in the lungs of mild (A) and severe IPF patients (B,C). Arrows denote staining present in alveolar macrophages (C) and hyperplastic alveolar epithelial cells (B). Scale bars=100 µm. Displayed sections are representative of n=10 (mild IPF) and n=10 (severe IPF).
Figure 4B:
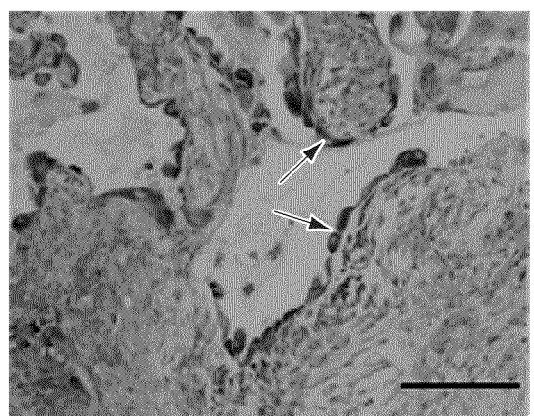
Figure 4C:
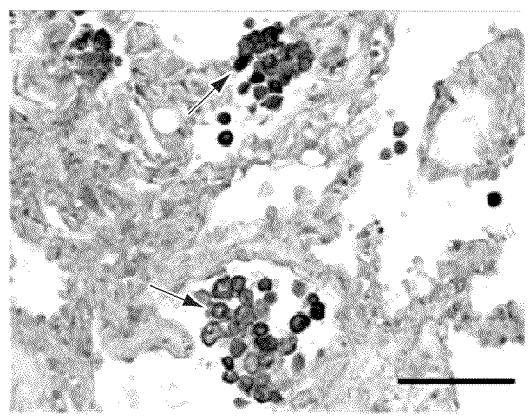

Immunolocalization was performed to determine cell types expressing cadherin-11 in lungs of patients with IPF using rabbit polyclonal anticadherin-11 antibodies. Mild IPF patients (FIG. 4A) had expression of cadherin-11 only on alveolar macrophages. The cell type expressing cadherin-11 identified in severe IPF patients was the alveolar macrophage (FIG. 4C) but also very prominent expression on the hyperplastic alveolar epithelial cells (AECs) adjacent to fibrotic foci (FIG. 4B). Together the data from FIGS. 3 and 4 indicate an association of cadherin-11 expression with disease severity and it is expressed on both hyperplastic AECs and alveolar macrophages in the lungs of affected patients.

Expression of Cadherin 11 in Bleomycin-Induced Mouse Model of Pulmonary Fibrosis.

Figure 5:
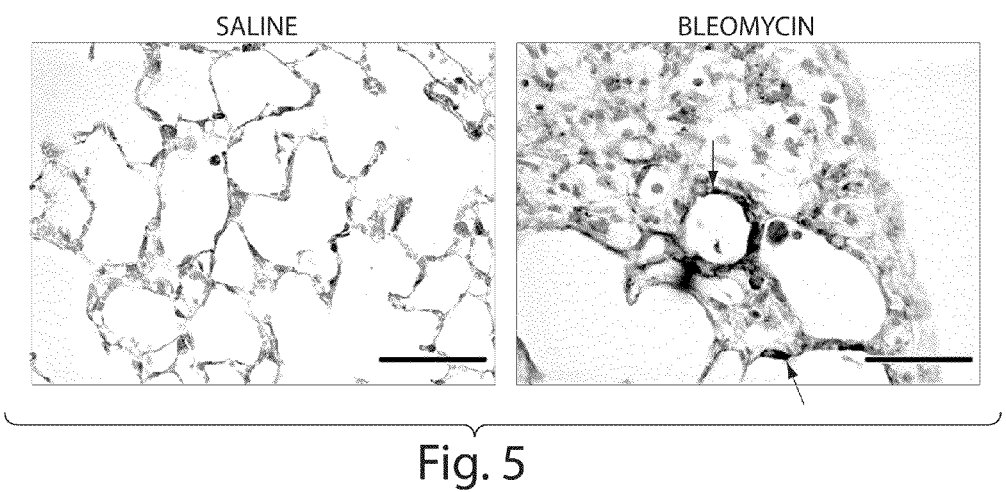
FIG. 5. Immunolocalization of cadherin-11 expression in the lungs of wild type mice administered intratracheal saline or bleomycin Arrows denote staining present in hyperplastic alveolar epithelial cells. Scale bars=50 µm. Displayed sections are representative of n=12 (saline) and n=20 (bleomycin).

The intratracheal bleomycin model is a commonly utilized animal model to study mechanisms of pulmonary fibrosis and idiopathic pulmonary fibrosis. To examine the role of cadherin-11 in this model, initial characterization was performed using immunolocalization for cadherin-11 in wild type mice given intratracheal saline or bleomycin. Similar to humans subjects with IPF, immunohistochemistry on lungs from mice given bleomycin displays prominent cadherin-11 expression in the hyperplastic AECs and alveolar macrophages (FIG. 5). These results demonstrate similarities between this mouse model and humans and support analysis of these cell types in addressing the mechanism of cadherin-11-dependent fibrosis.

Contribution of Cadherin-11 to Pulmonary Fibrosis.

Figure 6A:
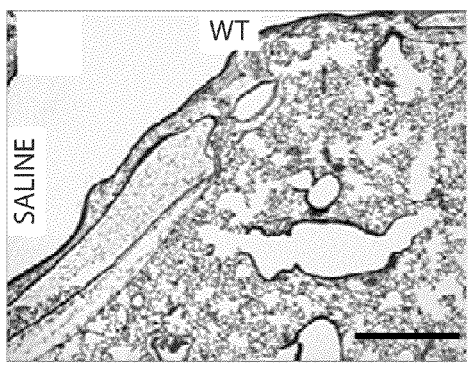
FIG. 6. Cadherin 11-dependent histopathology in pulmonary fibrosis. Lung histological sections from wild type and Cdh11$^{-/-}$ mice in the bleomycin-induced pulmonary fibrosis model. Lungs were taken from mice 21 days after 3.5 U bleomycin installation and processed for sectioning and H&E staining. (A) wild type mice administered intratracheal saline (n=6), (B) Cdh11$^{-/-}$ mice administered intratracheal saline (n=6), (C) Wild type mice administered intratracheal bleomycin (n=13), (D) Cdh11$^{-/-}$ mice administered intratracheal saline (n=11). Scale bars=500 µm. Sections are representative of n=6 WT saline, n=6 Cdh11$^{-/-}$ saline, n=13 WT bleomycin, n=11 Cdh11$^{-/-}$ bleomycin.
Figure 6B:
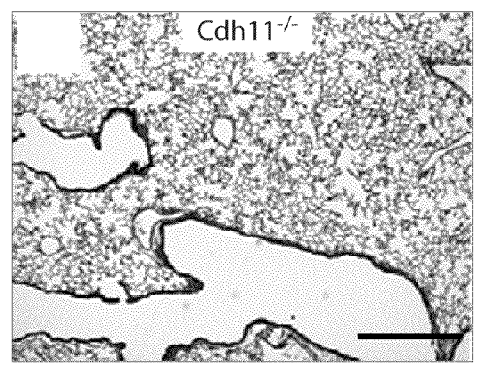
Figure 6C:
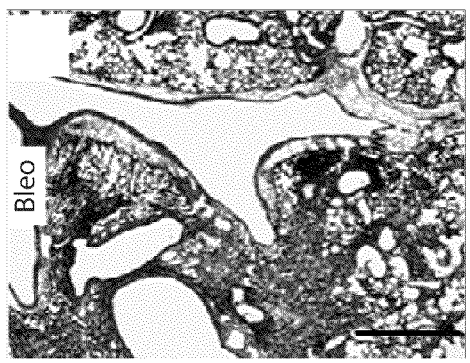
Figure 6D:
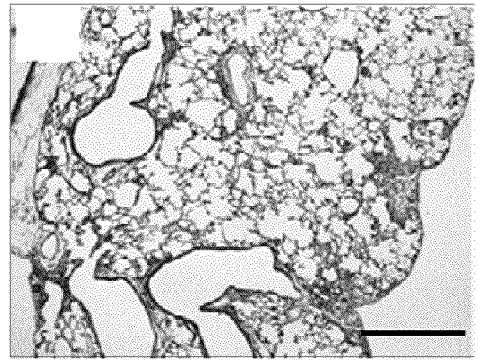

Given the increased expression of cadherin-11 in severe IPF lungs and lungs in the bleomycin lung fibrosis model, we next wanted to determine if cadherin-11 is involved with the development pulmonary fibrosis. To examine the contribution of cadherin-11 to pulmonary fibrosis, intratracheal bleomycin was administered to mice lacking cadherin-11 (Cdh11$^{-/-}$) and compared to wild type mice administered bleomycin. All endpoints were assessed at 21 days after bleomycin or saline installation. Results of H&E staining display no detectable difference in pulmonary histology between wild type (WT) and Cdh11$^{-/-}$ mice given saline (FIGS. 6A and B). Examination of lung sections from wild type (WT) mice given bleomycin displays standard histopathologic features consistent with pulmonary fibrosis including inflammation, fibrotic foci and disruption of normal alveolar architecture (FIG. 6C). These histologic endpoints are substantially reduced in Cdh11$^{-/-}$ mice (FIG. 6D).

Figure 7A:
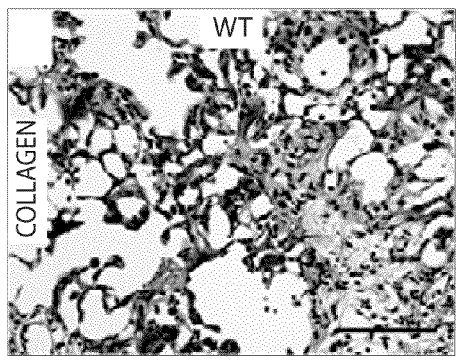
FIG. 7. Cadherin 11-dependent histopathology in pulmonary fibrosis. Lung histological sections from wild type and Cdh11$^{-/-}$ mice in the bleomycin-induced pulmonary fibrosis model. Lungs were taken from mice 21 days after 3.5 U bleomycin installation and processed for sectioning and Masson's trichrome stain (A,B) or IHC analyses for alpha smooth muscle actin, a marker for myofibroblasts (C,D). Scale bars=200 µm. Sections are representative of n=13 WT bleomycin, n=11 Cdh11$^{-/-}$ bleomycin.
Figure 7B:
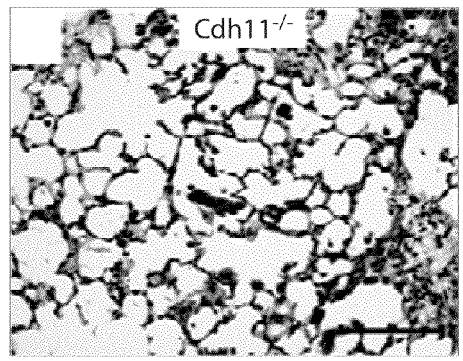
Figure 7C:
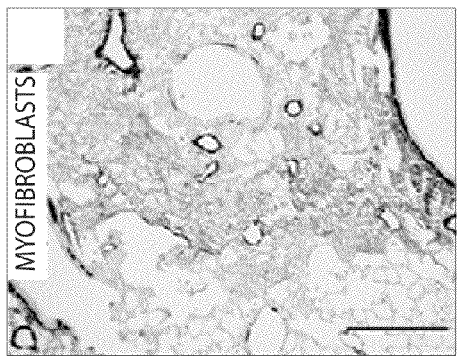
Figure 7D:
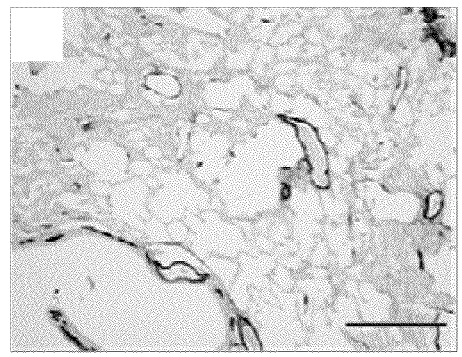

Masson's trichrome stain of histological sections (matrix stains blue, cells red) demonstrate increased collagen deposition in wild type mice administered bleomycin which is decreased in Cdh11$^{-/-}$ mice administered bleomycin (FIGS. 7A and B). IHC analyses for alpha-smooth muscle actin, a marker for myofibroblasts, was also performed. Myofibroblasts are a key cellular mediators in the pathogenesis of fibrosis that produce inflammatory cytokines and extracellular matrix. Wild type mice administered bleomycin had increased numbers of alpha-smooth muscle actin staining cells (FIG. 7C) while the number of alpha-smooth muscle actin staining cells of Cdh11$^{-/-}$ mice (FIG. 7D) was markedly decreased relative to wild type mice. The data in FIG. 7 support the hypothesis that cadherin-11 is a critical mediator of pulmonary fibrosis in this mouse model.

Figure 8A:
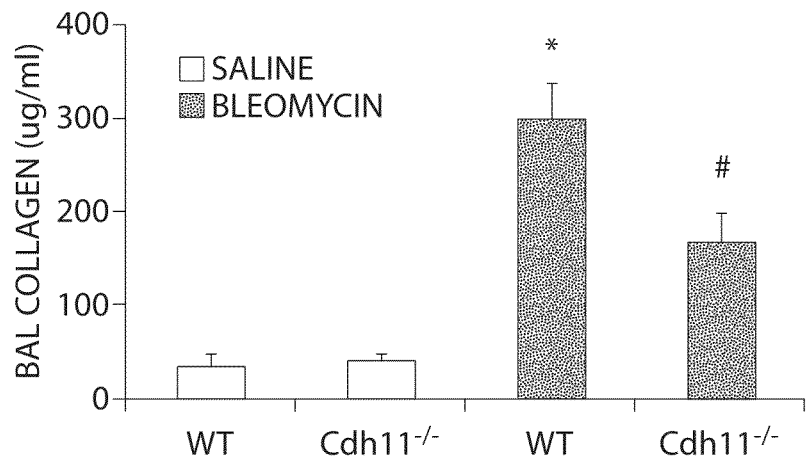
FIG. 8. Quantifiable fibrotic endpoints associated with genetic removal of Cdh11. Fibrosis was quantified by determination of (A) BAL collagen via colorimetric assay and (B) Ashcroft scoring on H&E stained lung sections. Scores were determined on 20 images per mouse lung. n=6 WT saline, n=6 Cdh11$^{-/-}$ saline, n=13 WT bleomycin, n=11 Cdh11$^{-/-}$ bleomycin. *P≤0.05 versus WT saline; #P≤0.05 versus WT bleomycin.
Figure 8B:
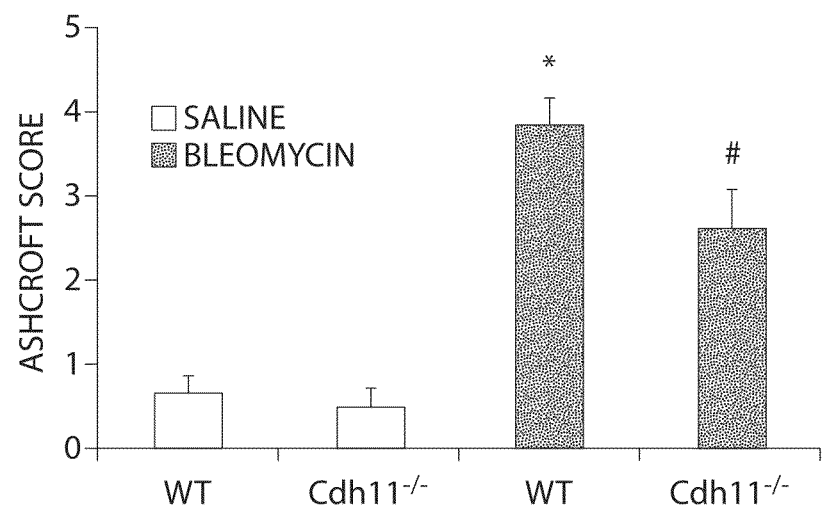

To further quantitate the attenuation in pulmonary fibrosis in the Cdh11$^{-/-}$ mice administered intratracheal bleomycin, collagen levels were determined using the Sircol assay in the bronchoalveolar (BAL) fluid from wild type and Cdh11$^{-/-}$ mice administered saline or bleomycin. As seen in FIG. 8A, intratracheal bleomycin significantly increased the amount of collagen in BAL fluid in wild type mice. In contrast, BAL fluid from Cdh11$^{-/-}$ mice administered bleomycin had a statistically significant decrease in collagen content relative to wild type mice. Lastly, we used the Ashcroft score, a commonly used scoring method to quantitate the amount of pulmonary fibrosis on H&E stained sections of lungs in the model. As seen in FIG. 8B, lungs from wild type mice administered intratracheal bleomycin significantly had a significantly higher score compared to lungs from Cdh11$^{-/-}$ mice administered bleomycin. Together the data from FIGS. 6-8 clearly demonstrate the cadherin-11 is a critical mediator of pulmonary fibrosis. Given the increased levels of cadherin-11 in human IPF lungs, these data suggest that cadherin-11 is a therapeutic target for pulmonary fibrosis.

Systemic Delivery of CDH11 Blocking Antibody Improves Established Pulmonary Fibrosis.

The data present in FIGS. 6-8 clearly demonstrate that Cdh11$^{-/-}$ mice have an attenuated pulmonary fibrotic response in the bleomycin induced fibrosis model. Although there are no gross histological differences in the lungs of wild type and Cdh11$^{-/-}$ mice, it is important to determine if blockade of cadherin-11 also decreases pulmonary fibrosis. Furthermore, it is of interest to determine if cadherin-11 blockade is effective in the treatment of pulmonary fibrosis and not only in preventing the development of fibrosis as suggested by the Cdh11$^{-/-}$ mice studies. Pulmonary fibrosis in the bleomycin model is established at least 7 days after bleomycin installation (A. Moeller et al., Int Journal of Biochem and Cell Biol. 2008). Therefore, to determine if mice with established fibrosis can be successfully treated by targeting cadherin-11, wild type mice were administered one of two systemic cadherin-11 blocking antibodies (clone 23C6 or 13C2) beginning 10 days after bleomycin installation.

Figure 9:
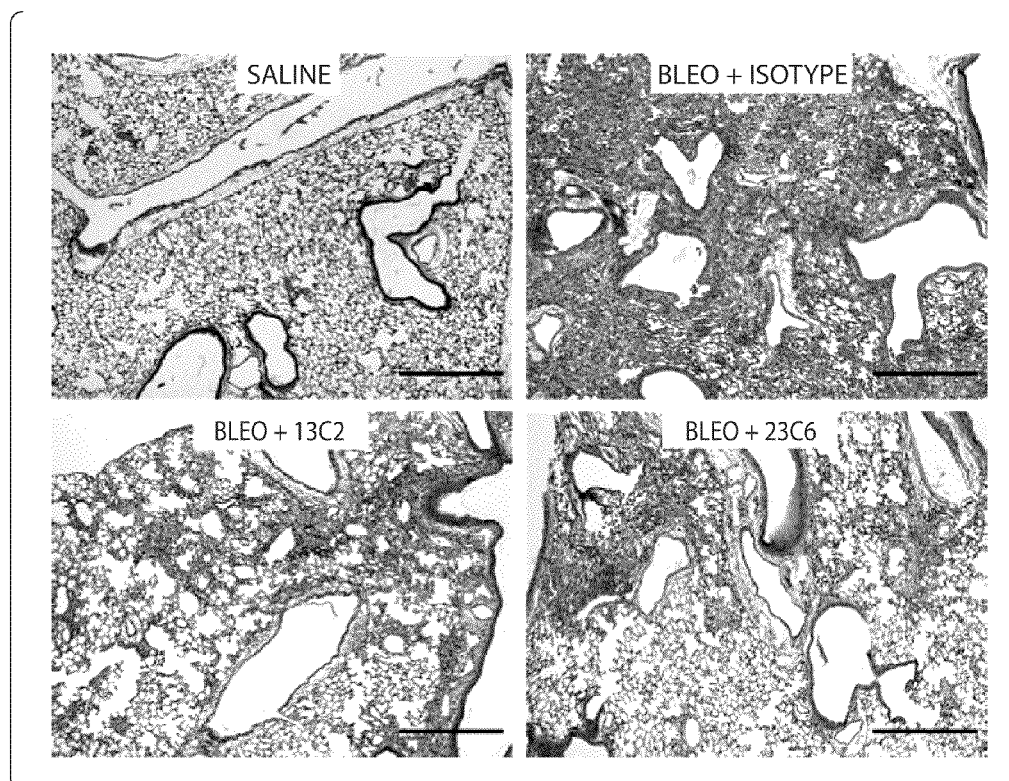
FIG. 9. Cadherin-11 blocking antibodies improves established pulmonary fibrosis. Histopathologic improvement was noted in bleomycin-induced pulmonary fibrosis associated with systemic delivery of cadherin-11 blocking antibodies (23C6 or 13C2) compared with isotype control. Mice received antibody every other day beginning 10 days after bleomycin exposure. Lungs were then taken at day 21 and processed for sectioning and H&E staining. Scale bars=500 µm. Sections are representative of n=6 saline, n=7 Bleo+isotype, n=8 Bleo+13C2, and n=6 Bleo+23C6.

Wild type mice were administered intratracheal bleomycin. On day 10, when fibrosis is already established, the mice were administered 500 ug of either 23C6, 13C2, or isotype control antibody via the intraperitoneal route followed by 100 ug of antibodies IP every other day until day 21. Mice were sacrificed and lungs were processed for histology. Lung sections, stained with H&E (FIG. 9), demonstrated that wild type mice administered bleomycin and isotype antibodies developed pulmonary fibrosis which was markedly attenuated in the wild type mice that received bleomycin followed by IP 23C6 or 13C2 starting on day 10.

Figure 10A:
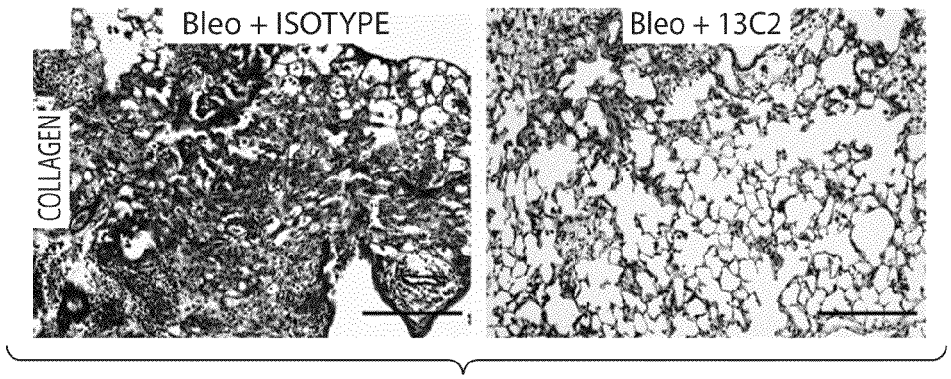
FIG. 10. Cadherin-11 blocking antibody reduces lung collagen and myofibroblasts. Mouse lungs given bleomycin plus systemic antibody were processed and stained for (A) collagen deposition (Masson's Trichrome stain) and (B) myofibroblasts (a-SMA immunohistochemistry). Scale bars=200 µm. (C) Soluble collagen in BAL fluid quantified with colorimetric assay. n=6 saline, n=7 Bleo+isotype, n=8 Bleo+13C2, and n=6 Bleo+23C6. *P≤0.05 versus saline; #P≤0.05 versus bleomycin+isotype.
Figure 10B:
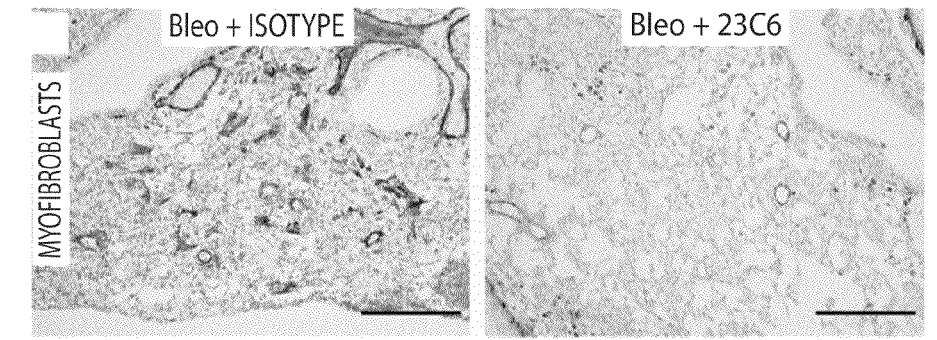
Figure 10C:
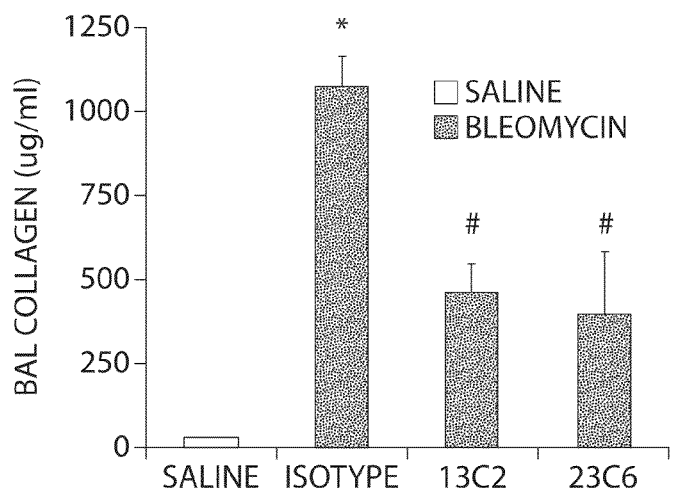
Figure 11A:
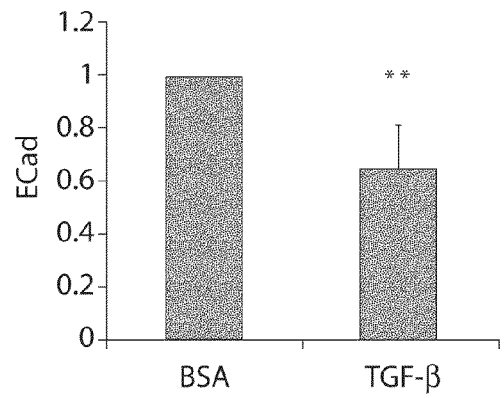
FIG. 11. TGF-β-induced EMT and Cdh11 expression in A549 lung epithelial cells. A549 lung epithelial cells were stimulated with TGF-β (10 ng/ml) and at 24 hours, RNA was isolated and fold change transcripts (vs. BSA) were determined for (A) E cadherin, (B) N cadherin, (C) α1 pro-collagen, and (D) cadherin 11. *P<0.05 versus BSA. **P=0.06 versus BSA. Data representative of 3 separate experiments.
Figure 11B:
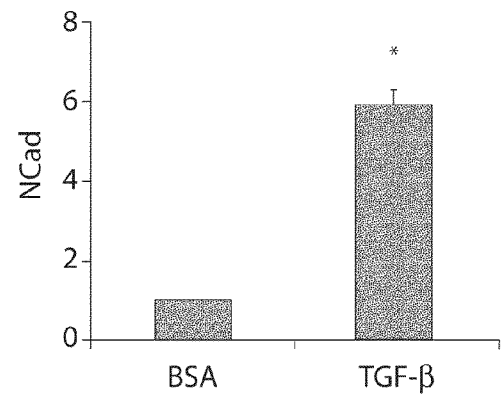
Figure 11C:
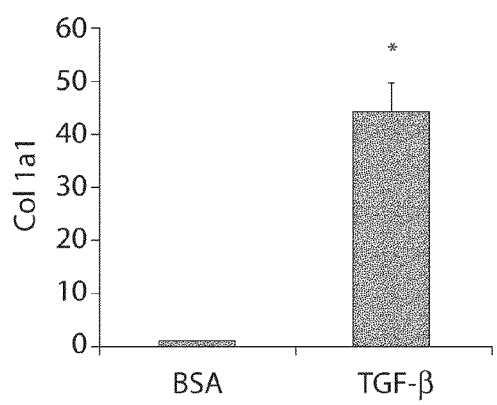
Figure 11D:
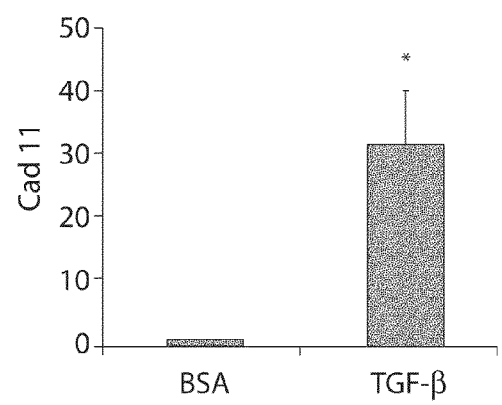
Figure 12A:
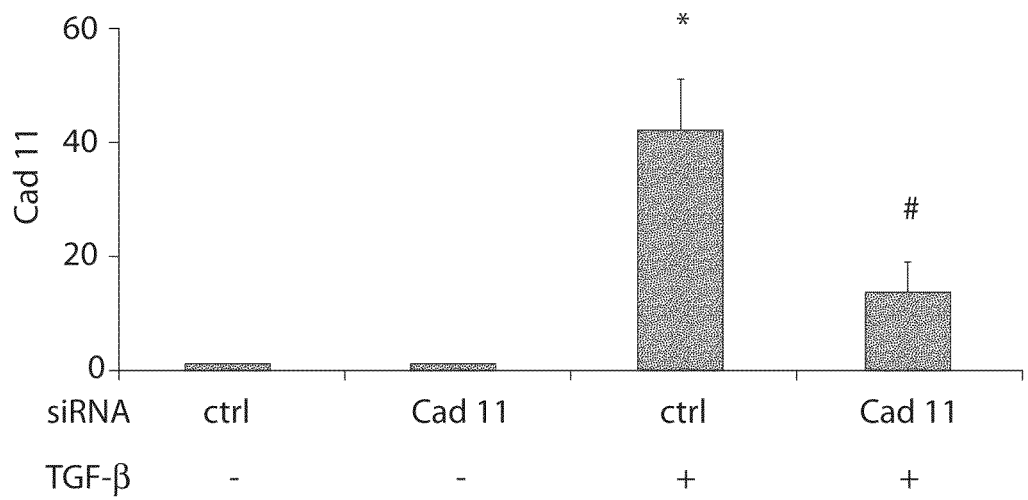
FIG. 12. Cdh11 knockdown prevents TGF-β-induced EMT of lung epithelial cells. A549 lung epithelial cells were transfected with Cdh11 or control siRNA, subsequently stimulated with TGF-β and at 24 hours, RNA was isolated and fold change transcripts (vs. BSA+control siRNA) were determined for (A) E cadherin, (B) N cadherin, (C) ca procollagen, and (D) cadherin-11. Data representative of 3 separate experiments.
Figure 12B:
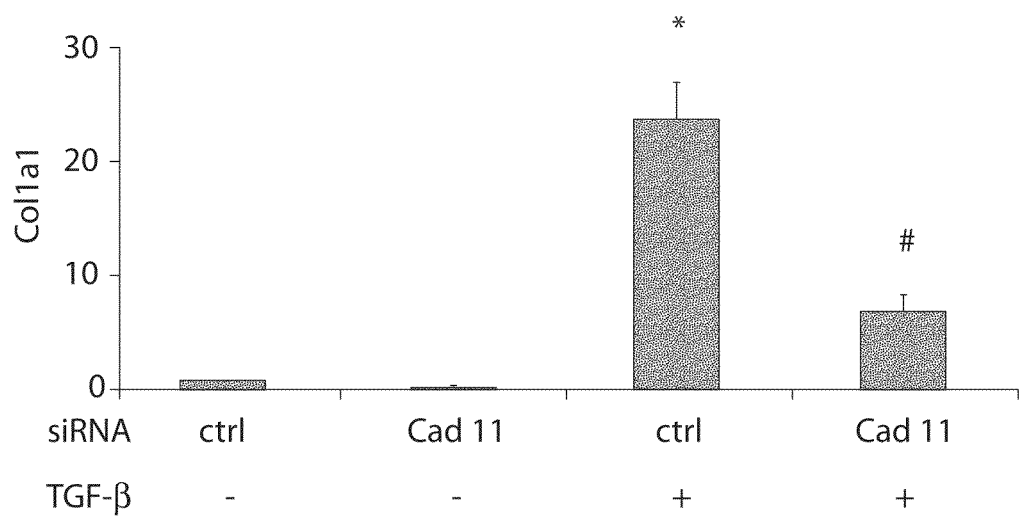
Figure 12C:
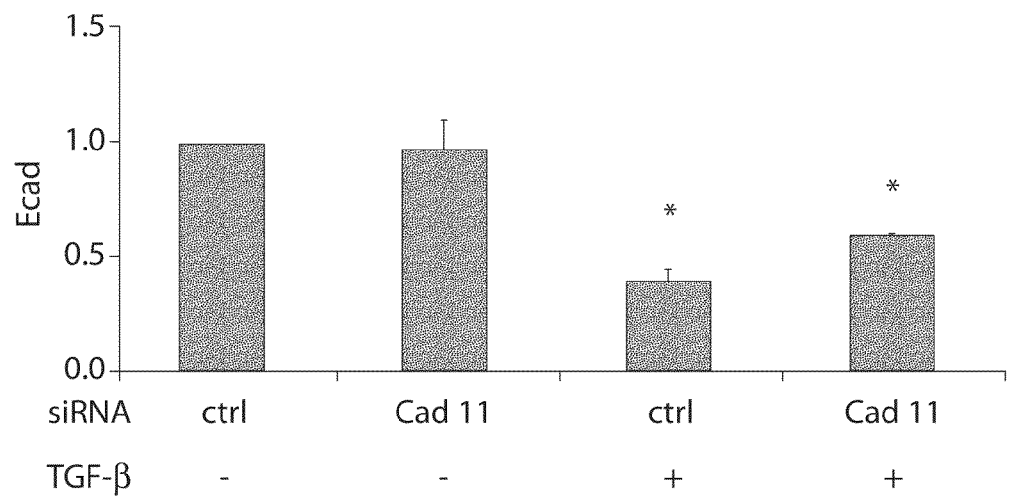
Figure 12D:
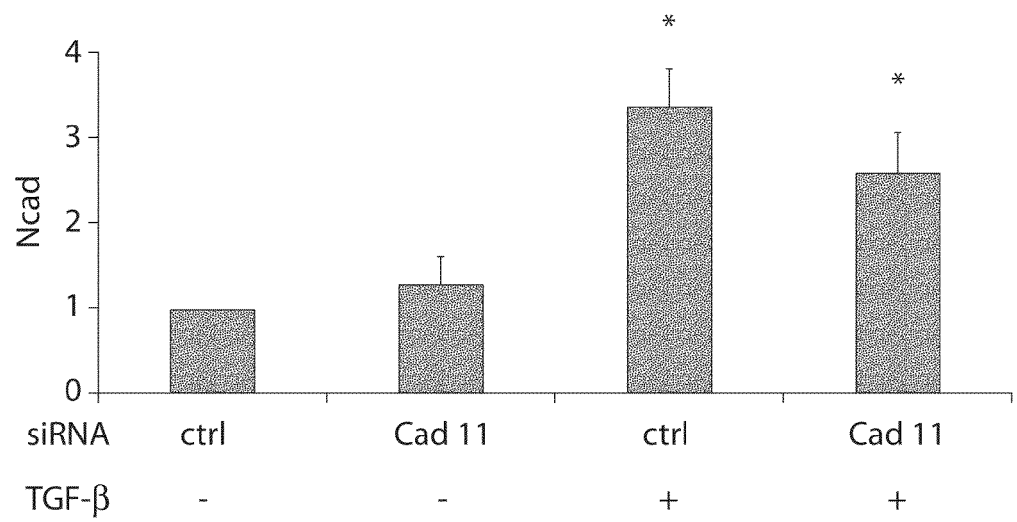

Additional analyses in these experiments confirmed the ability of 23C6 and 13C2 to treat existing pulmonary fibrosis in the bleomycin model. As seen in FIG. 10, lung sections, stained with Masson's Trichrome demonstrated that lungs from wild type mice administered bleomycin and isotype antibodies developed marked increased deposition of the extracellular matrix which was markedly attenuated in the wild type mice that received bleomycin followed by IP 23C6 or 13C2 starting on day 10. In addition, staining the alpha smooth muscle actin, the marker of the myofibroblast demonstrated that the anti-cadherin-11 monoclonal antibodies, 13C2 and 23C6, effectively reduced the number of myofibroblasts in the lungs of mice administered intratracheal bleomycin compared to isotype control antibodies. Finally, soluble collagen levels as determined by the Sircol assay on BAL fluid from mice treated with 13C2 or 23C6 anti-cadherin-11 monoclonal antibodies were significantly reduced compared to mice given isotype control antibodies. These results confirm findings in Cdh11$^{-/-}$ mice that CDH11 contributes to pulmonary fibrosis and demonstrates systemic delivery of cadherin-11 blocking antibody successfully treats established pulmonary fibrosis in the bleomycin induced fibrosis model.

Epithelial-to-Mesenchymal Transition (EMT).

Figure 13:
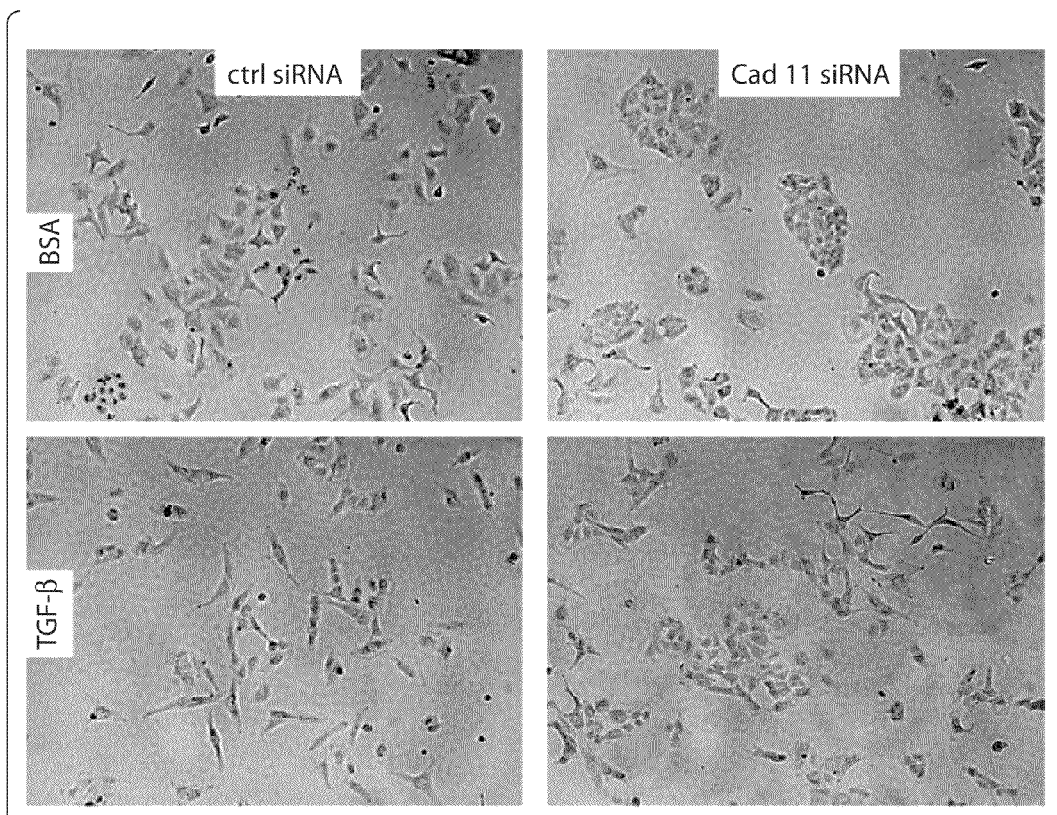
FIG. 13. Cdh11 knockdown prevents TGF-β-induced transition to mesenchymal morphology in lung epithelial cells. A549 lung epithelial cells were transfected with Cdh11 or control siRNA and subsequently stimulated with TGF-β. At 24 hours, cell morphology was assessed using phase contrast microscopy.
Figure 14:
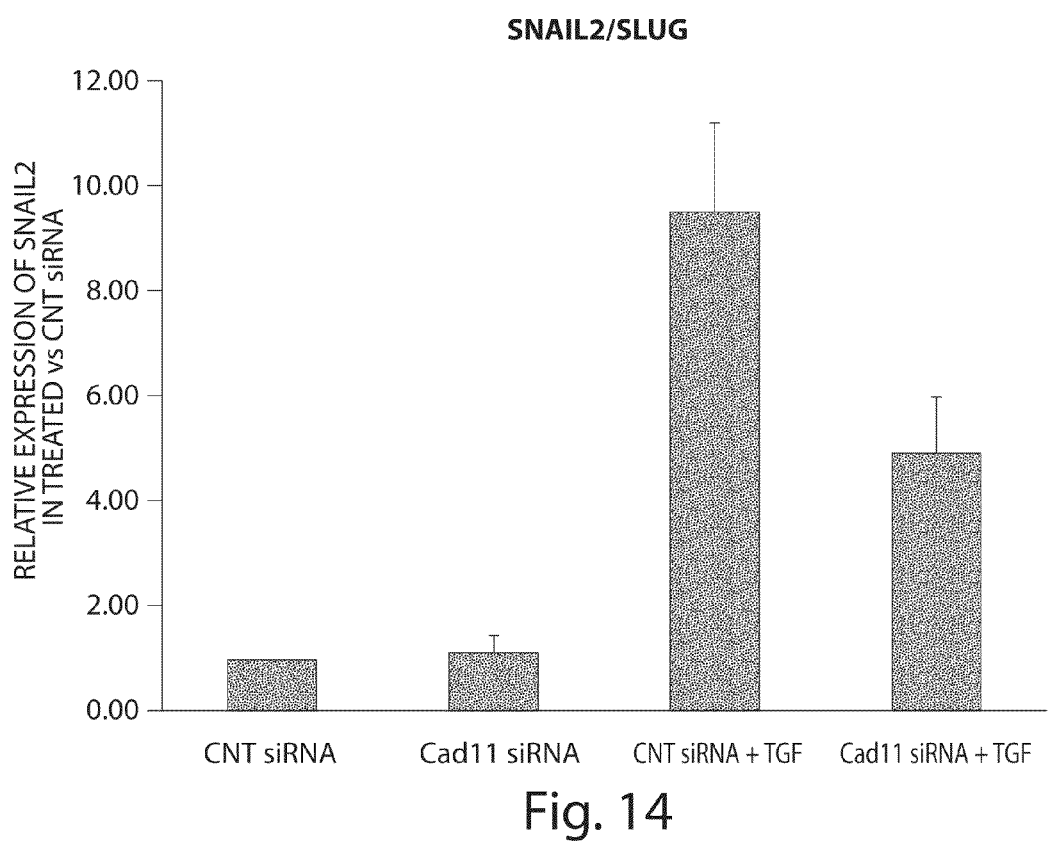
FIG. 14. Cdh11 knockdown prevents TGF-β-induced SNAIL2 upregulation in lung epithelial cells. A549 lung epithelial cells were transfected with Cdh11 or control siRNA, subsequently stimulated with TGF-β and at 24 hours, RNA was isolated and fold change transcripts (vs. BSA+control siRNA) were determined for SNAIL2, an EMT transcription factor. Data representative of 3 separate experiments.

EMT is involved in the pathogenesis of non-dermal fibrosis, and TGFbeta may play an role in this transition process. It is known that during EMT, expression of E-cadherin is reduced and/or eliminated. FIG. 11 shows that TGFbeta increases the expression of cadherin-11 in A549 cells, a lung epithelial cell line. In addition, expression of Col1a1 is increased, expression of E-cadherin is decreased (as expected), and expression of N-cadherin is also increased. FIGS. 12 and 13 show that when cadherin-11 expression is blocked in A549 cells, for example using a canderin-11 specific siRNA, and then the cells are stimulated with TGFbeta, the upregulation of Col1a1 expression by TGFbeta is dramatically reduced. Furthermore, using phase contrast microscopy, it is clear that the cadherin-11 knock down with siRNA prevents the development of the mesenchymal phenotype induced by TGFbeta. In the presence of TGFbeta, A549 cells lose cell-to-cell contacts, become spindle shaped, and spread out. Reduction in the level of cadherin-11 with siRNA prevents these phenotypic changes, suggesting that cadherin-11 siRNA blocks EMT and that cadherin-11 is involved in and potentially mediating EMT. FIG. 14 further shows that cadherin-11 also blocks the TGFbeta-induced upregulation of SNAIL2, a key EMT transcription factor.

REFERENCES

1. Mayes M D, Lacey J V, Jr., Beebe-Dimmer J et al. Prevalence, incidence, survival, and disease characteristics of systemic sclerosis in a large US population. Arthritis Rheum 2003; 48(8):2246-2255.
2. Wilson L. Cost-of-illness of scleroderma: the case for rare diseases. Semin Arthritis Rheum 1997; 27(2):73-84.
3. Thannickal V J, Toews G B, White E S, Lynch J P, III, Martinez F J. Mechanisms of pulmonary fibrosis. Annu Rev Med 2004; 55:395-417.
4. Sime P J, O'Reilly K M. Fibrosis of the lung and other tissues: new concepts in pathogenesis and treatment. Clin Immunol 2001; 99(3):308-319.
5. Wagner G R. Asbestosis and silicosis. Lancet 1997; 349 (9061):1311-1315.
6. Vanhee D, Gosset P, Wallaert B, Voisin C, Tonnel A B. Mechanisms of fibrosis in coal workers' pneumoconiosis. Increased production of platelet-derived growth factor, insulin-like growth factor type I, and transforming growth factor beta and relationship to disease severity. Am J Respir Crit Care Med 1994; 150(4):1049-1055.
7. Abid S H, Malhotra V, Perry M C. Radiation-induced and chemotherapy-induced pulmonary injury. Curr Opin Oncol 2001; 13(4):242-248.
8. Steen V D, Owens G R, Fino G J, Rodnan G P, Medsger T A, Jr. Pulmonary involvement in systemic sclerosis (scleroderma). Arthritis Rheum 1985; 28(7):759-767.
9. Majumdar S, Li D, Ansari T et al. Different cytokine profiles in cryptogenic fibrosing alveolitis and fibrosing alveolitis associated with systemic sclerosis: a quantitative study of open lung biopsies. Eur Respir J 1999; 14(2):251-257.
10. Lewis M J, Lewis E H, III, Amos J A, Tsongalis G J. Cystic fibrosis. Am J Clin Pathol 2003; 120 Suppl:S3-13.
11. Elias J A, Lee C G, Zheng T, Ma B, Horner R J, Zhu Z. New insights into the pathogenesis of asthma. J Clin Invest 2003; 111(3):291-297.
12. Coultas D B, Zumwalt R E, Black W C, Sobonya R E. The epidemiology of interstitial lung diseases. Am J Respir Crit Care Med 1994; 150(4):967-972.
13. Raghu G, Weycker D, Edelsberg J, Bradford W Z, Oster G. Incidence and prevalence of idiopathic pulmonary fibrosis. Am J Respir Crit Care Med 2006; 174(7):810-816.
14. Panos R J, Mortenson R L, Niccoli S A, King T E, Jr. Clinical deterioration in patients with idiopathic pulmonary fibrosis: causes and assessment. Am J Med 1990; 88(4):396-404.
15. Selman M, King T E, Pardo A. Idiopathic pulmonary fibrosis: prevailing and evolving hypotheses about its pathogenesis and implications for therapy. Ann Intern Med 2001; 134(2):136-151.
16. Preliminary criteria for the classification of systemic sclerosis (scleroderma). Subcommittee for scleroderma criteria of the American Rheumatism Association Diagnostic and Therapeutic Criteria Committee. Arthritis Rheum 1980; 23(5):581-590.

17. Lee D M, Kiener H P, Agarwal S K et al. Cadherin-11 in synovial lining formation and pathology in arthritis. Science 2007; 315(5814):1006-1010.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method for treating a subject having lung fibrosis comprising
administering to a subject in need thereof an anti-cadherin-11 antibody or an antigen-binding fragment thereof in an amount effective to reduce lung fibrosis.

2. The method of claim 1, wherein lung fibrosis is idiopathic pulmonary fibrosis.

3. The method of claim 2, wherein idiopathic pulmonary fibrosis is severe idiopathic pulmonary fibrosis.

4. The method of claim 1, wherein the anti-cadherin-11 antibody or the antigen-binding fragment thereof is administered by inhalation or intranasally.

5. The method of claim 1, wherein the anti-cadherin-11 antibody or the antigen-binding fragment thereof is administered intraperitoneally.

6. The method of claim 1, further comprising administering to the subject an immunosuppressant.

7. The method of claim 6, wherein the immunosuppressant is a steroid.

* * * * *